(12) United States Patent
Mackowiak et al.

(10) Patent No.: US 11,608,483 B2
(45) Date of Patent: Mar. 21, 2023

(54) INVERTED CULTURE PLATE SYSTEM FOR CELLULAR CO-CULTURE

(71) Applicant: University of Maryland, Baltimore, Baltimore, MD (US)

(72) Inventors: Bryan Mackowiak, Cary, NC (US); Hongbing Wang, Ellicott City, MD (US); Linhao Li, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1084 days.

(21) Appl. No.: 16/315,753

(22) PCT Filed: Jul. 7, 2017

(86) PCT No.: PCT/US2017/041054
§ 371 (c)(1),
(2) Date: Jan. 7, 2019

(87) PCT Pub. No.: WO2018/009767
PCT Pub. Date: Jan. 11, 2018

(65) Prior Publication Data
US 2019/0249126 A1    Aug. 15, 2019

Related U.S. Application Data

(60) Provisional application No. 62/359,367, filed on Jul. 7, 2016.

(51) Int. Cl.
| | | |
|---|---|---|
| C12M 1/32 | (2006.01) |
| C12M 3/06 | (2006.01) |
| C12M 1/12 | (2006.01) |
| C12M 3/00 | (2006.01) |
| B01L 3/00 | (2006.01) |
| C12M 1/00 | (2006.01) |
| C12N 5/00 | (2006.01) |

(52) U.S. Cl.
CPC ......... *C12M 23/12* (2013.01); *B01L 3/50853* (2013.01); *C12M 1/12* (2013.01); *C12M 3/00* (2013.01); *C12M 3/06* (2013.01); *C12M 23/34* (2013.01); *C12M 25/04* (2013.01); *C12N 5/0018* (2013.01); *B01L 2300/047* (2013.01); *B01L 2300/0829* (2013.01); *B01L 2300/0858* (2013.01); *B01L 2300/163* (2013.01)

(58) Field of Classification Search
None
See application file for complete search history.

(56) References Cited

U.S. PATENT DOCUMENTS 5,759,851 A * 6/1998 Mathus ................. C12M 25/04
435/297.1
5,801,055 A * 9/1998 Henderson .......... B01L 3/50255
422/536

* cited by examiner

*Primary Examiner* — Erin M. Bowers
(74) *Attorney, Agent, or Firm* — Riverside Law LLP

(57) ABSTRACT

The present invention provides improved devices for co-culture of cells. The devices include inserts having invertible wells that can be lowered into a well of any standard cell culture plate. A first population of cells can be cultured in the invertible wells of the inserts and a second population of cells can be cultured in the wells of a cell culture plate. Once the first population of cells attach to the invertible wells, the inserts are flipped over and placed into the wells of the cell culture plate to co-culture with the second population of cells.

14 Claims, 29 Drawing Sheets
Specification includes a Sequence Listing.

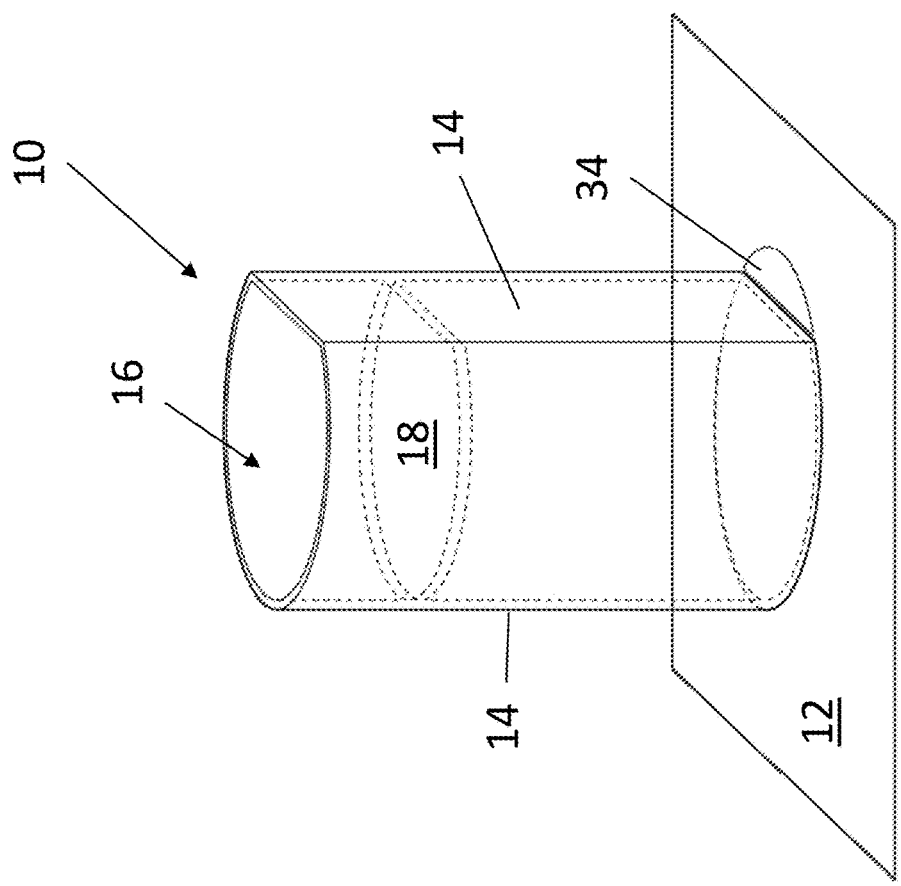
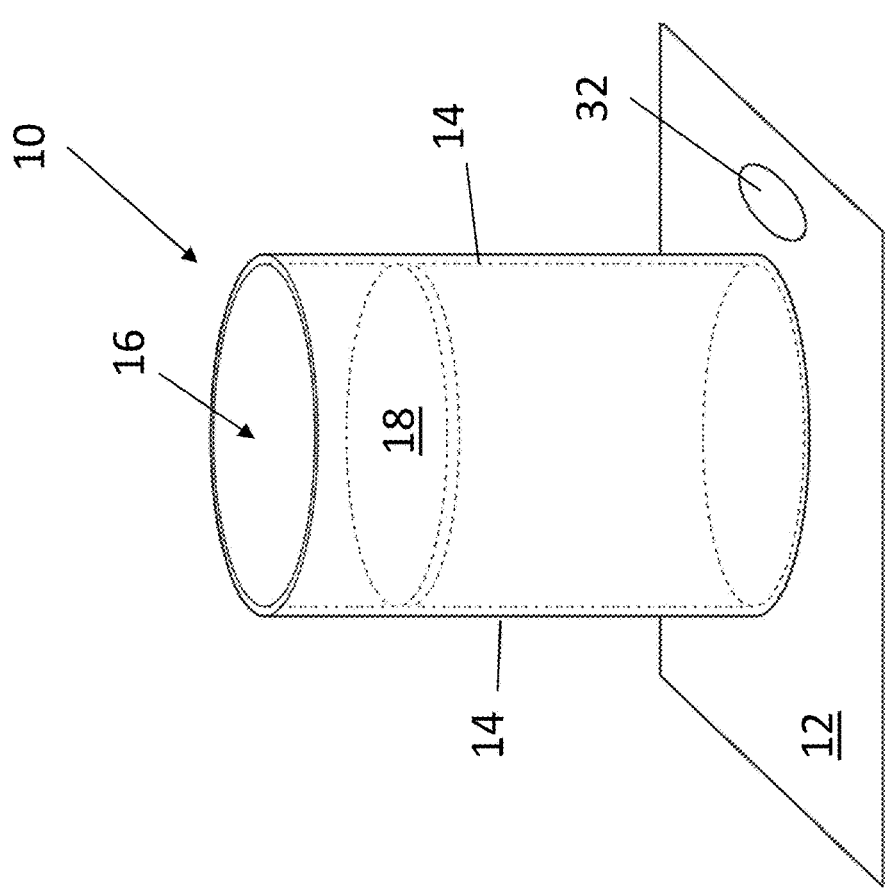

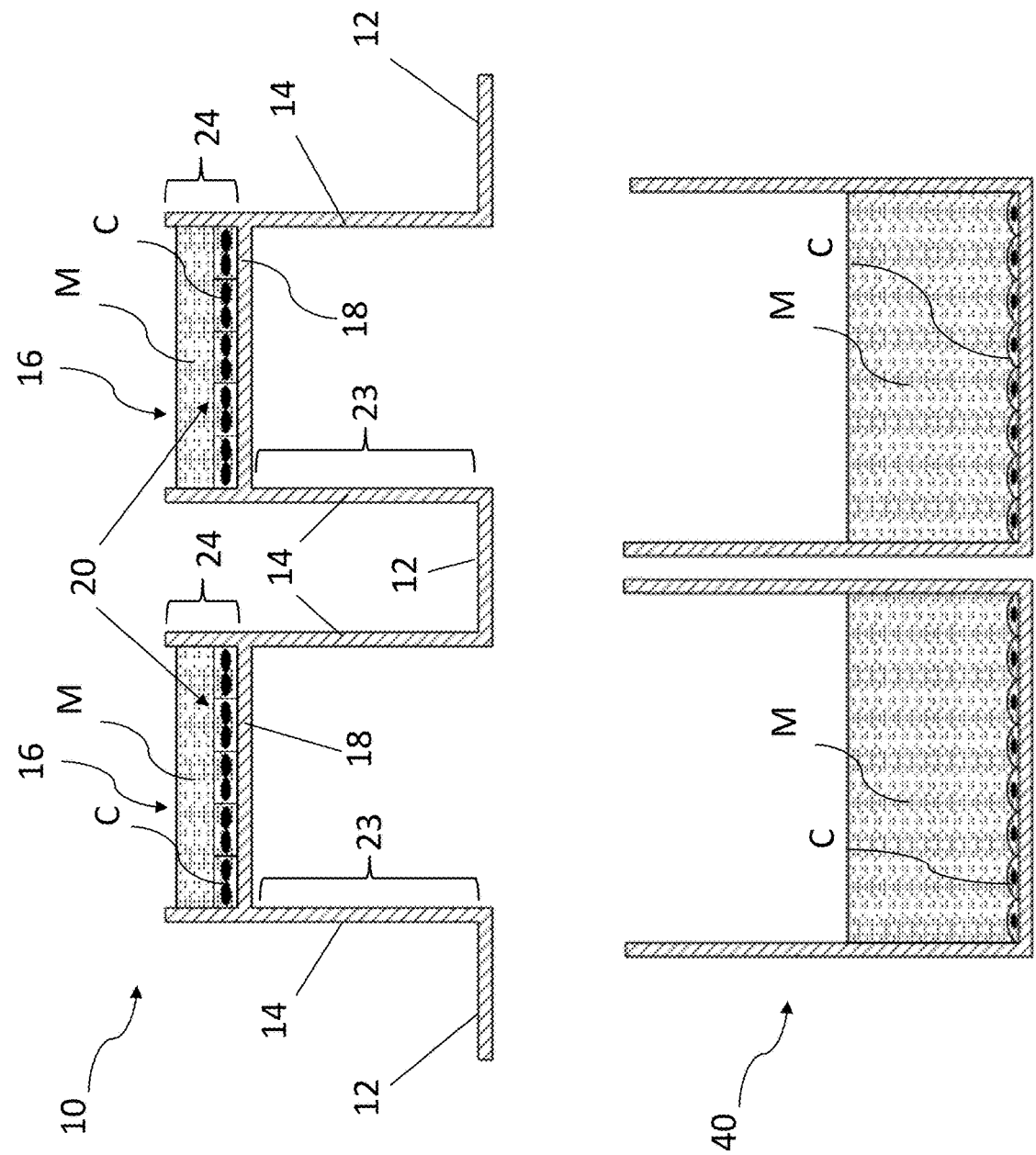

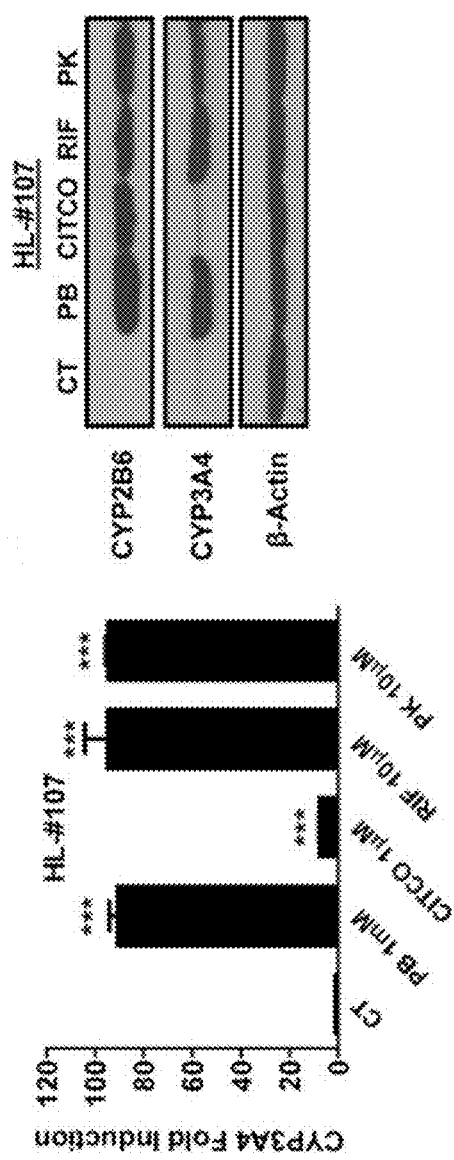
Figure 9A
Figure 9B
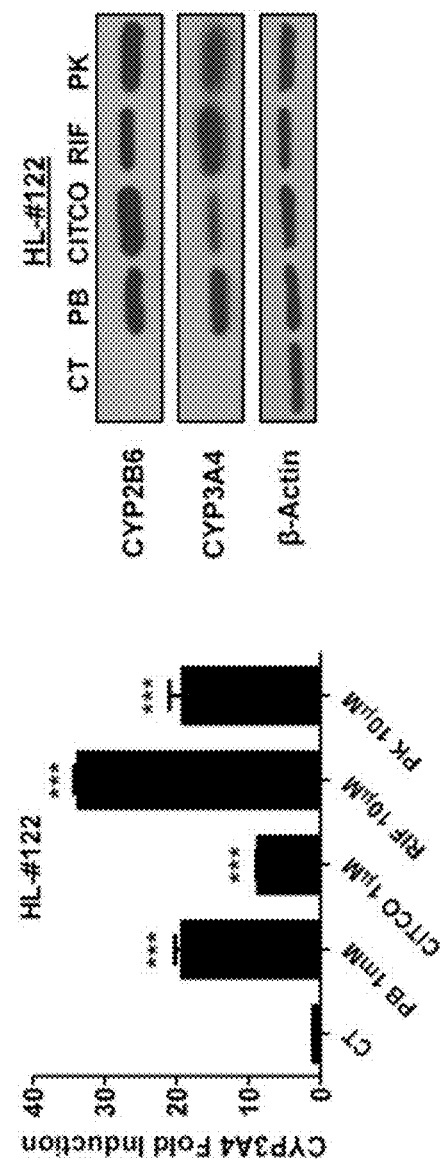
Figure 9D
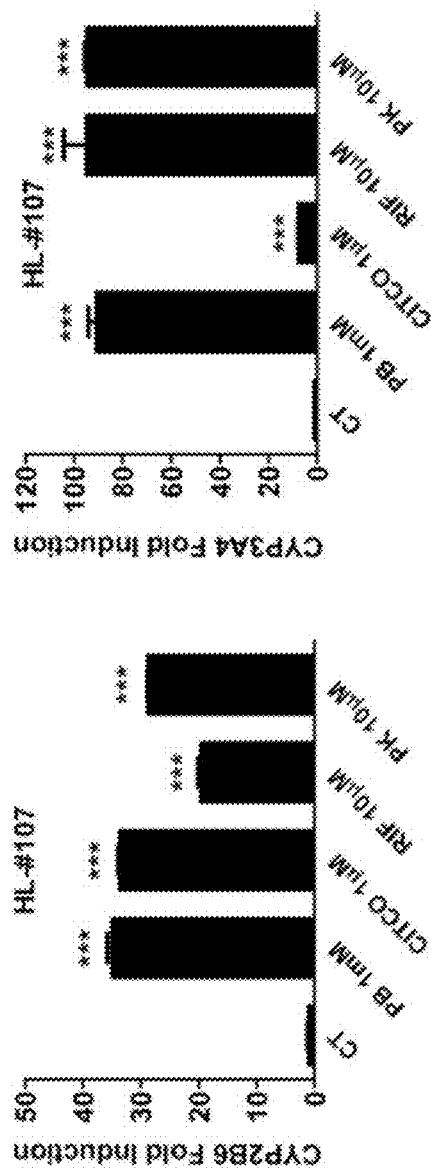
Figure 9C
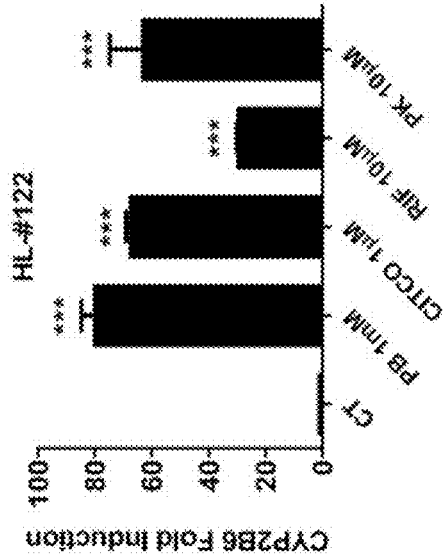

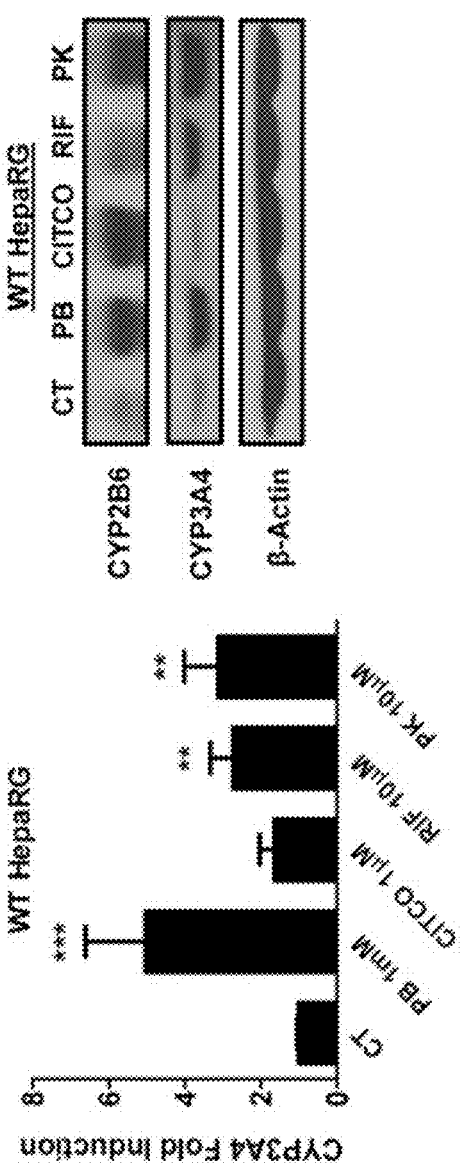
Figure 10A
Figure 10B
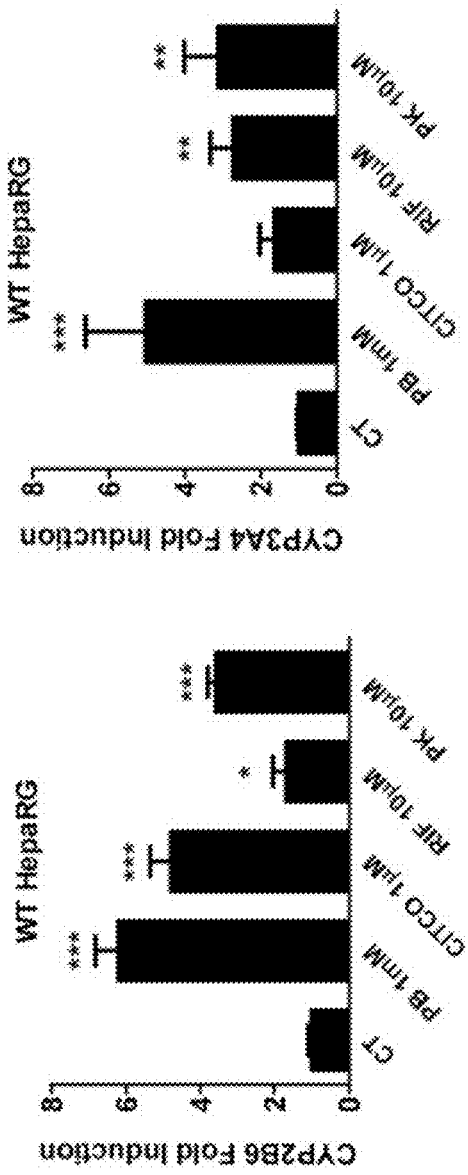
Figure 10C
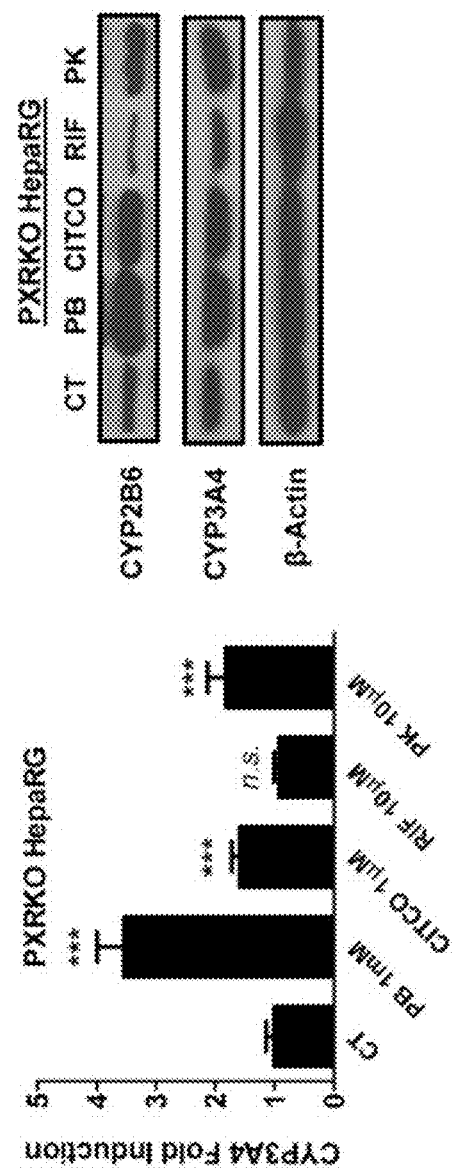
Figure 10D

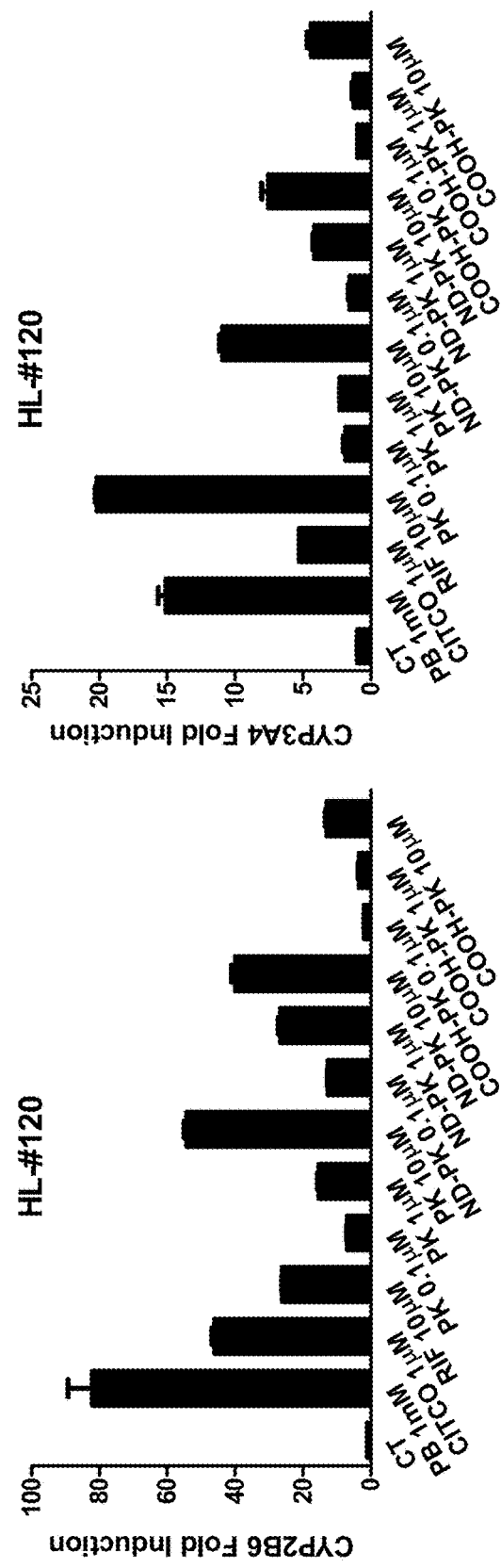
Figure 14A
Figure 14B
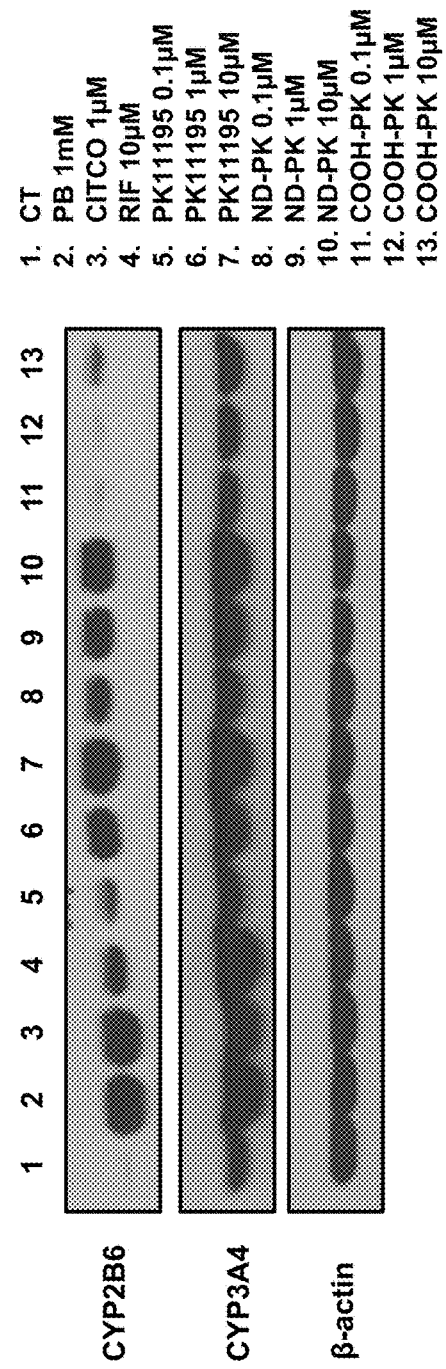

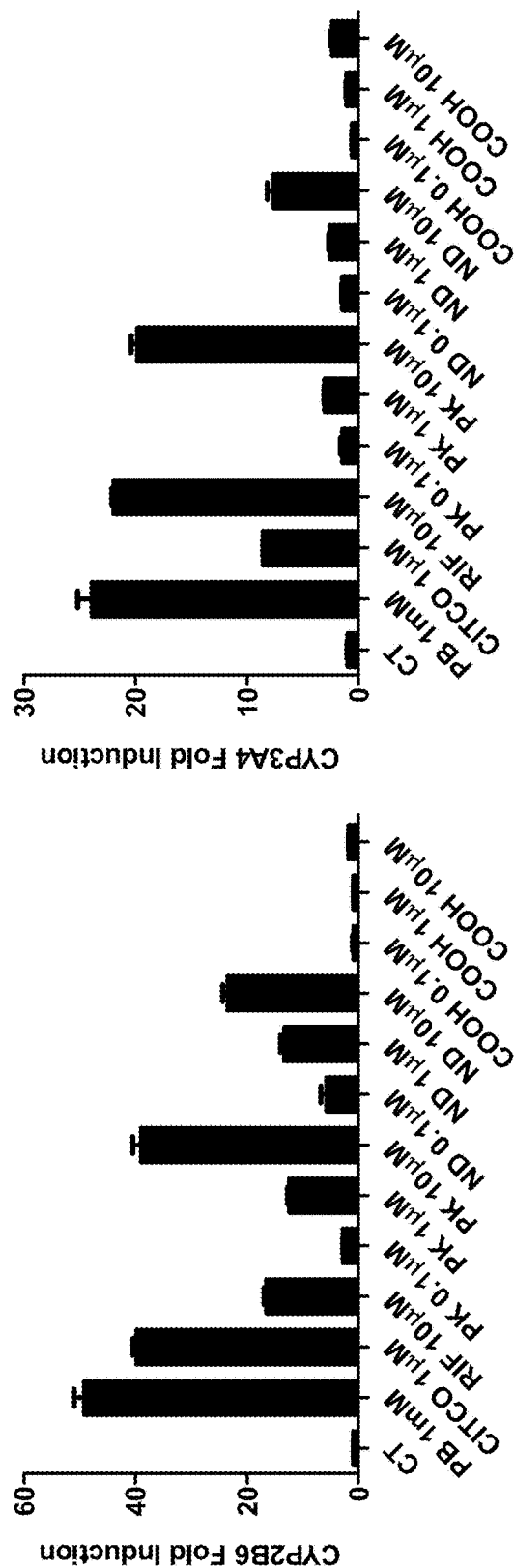
Figure 14C
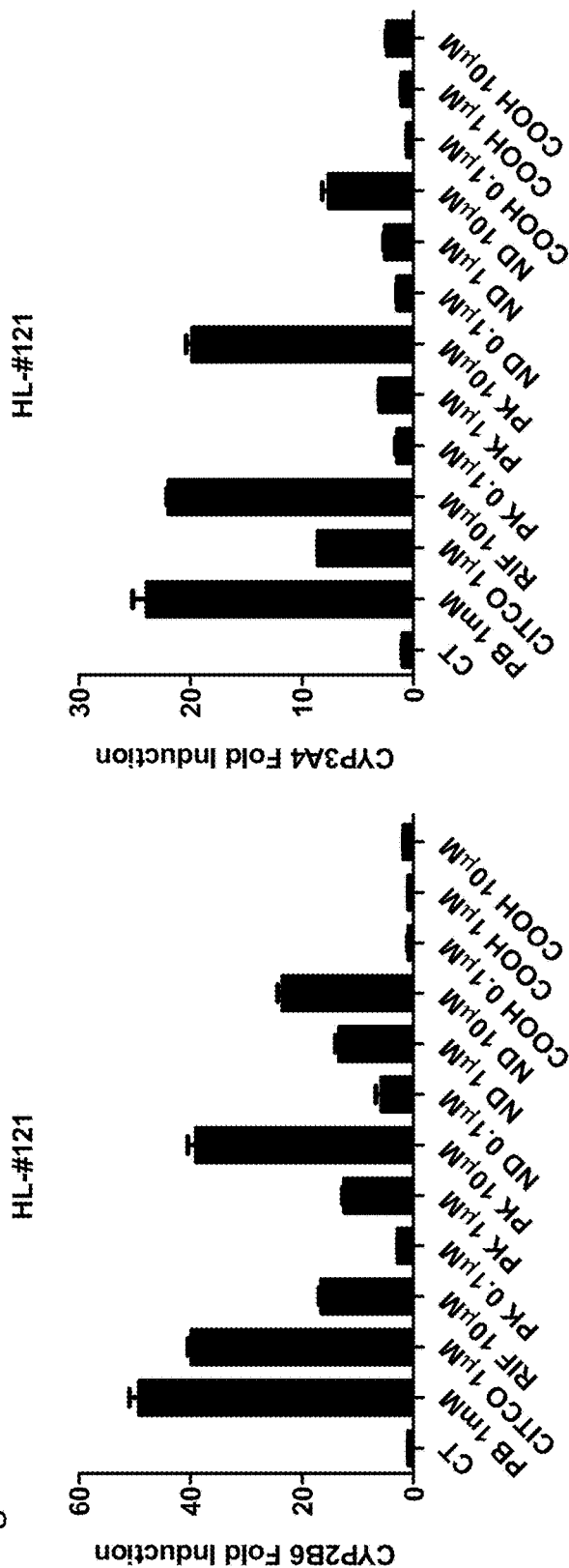
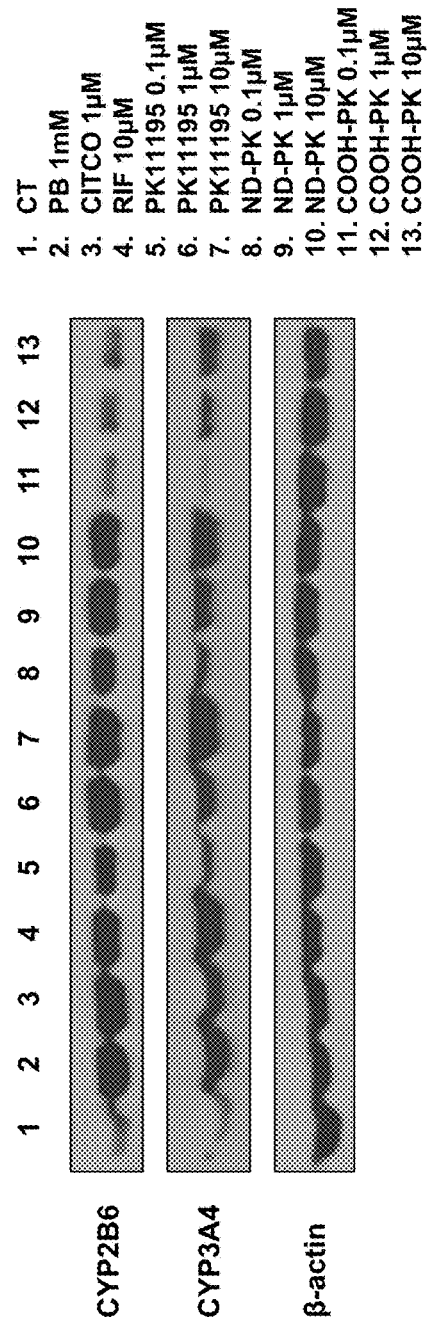
Figure 14D

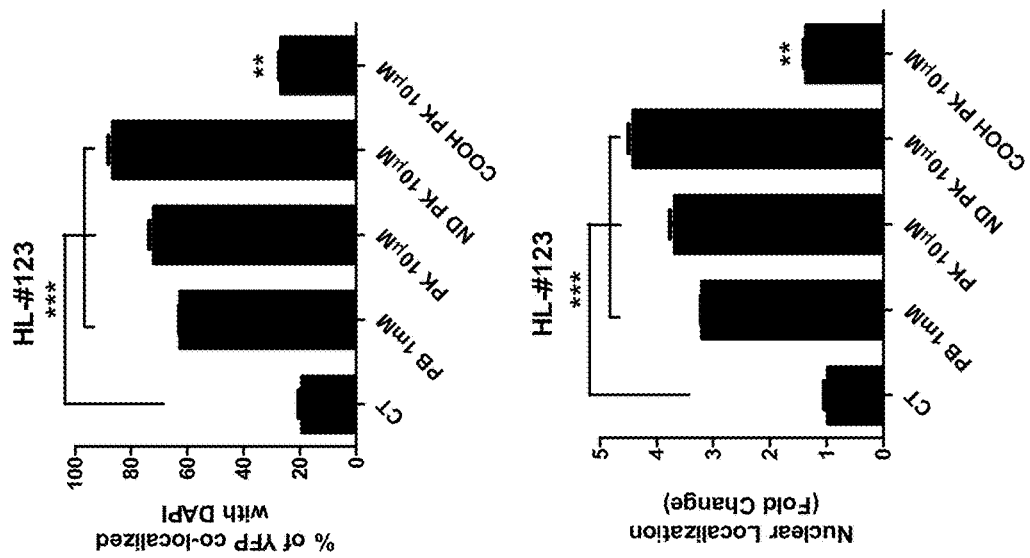
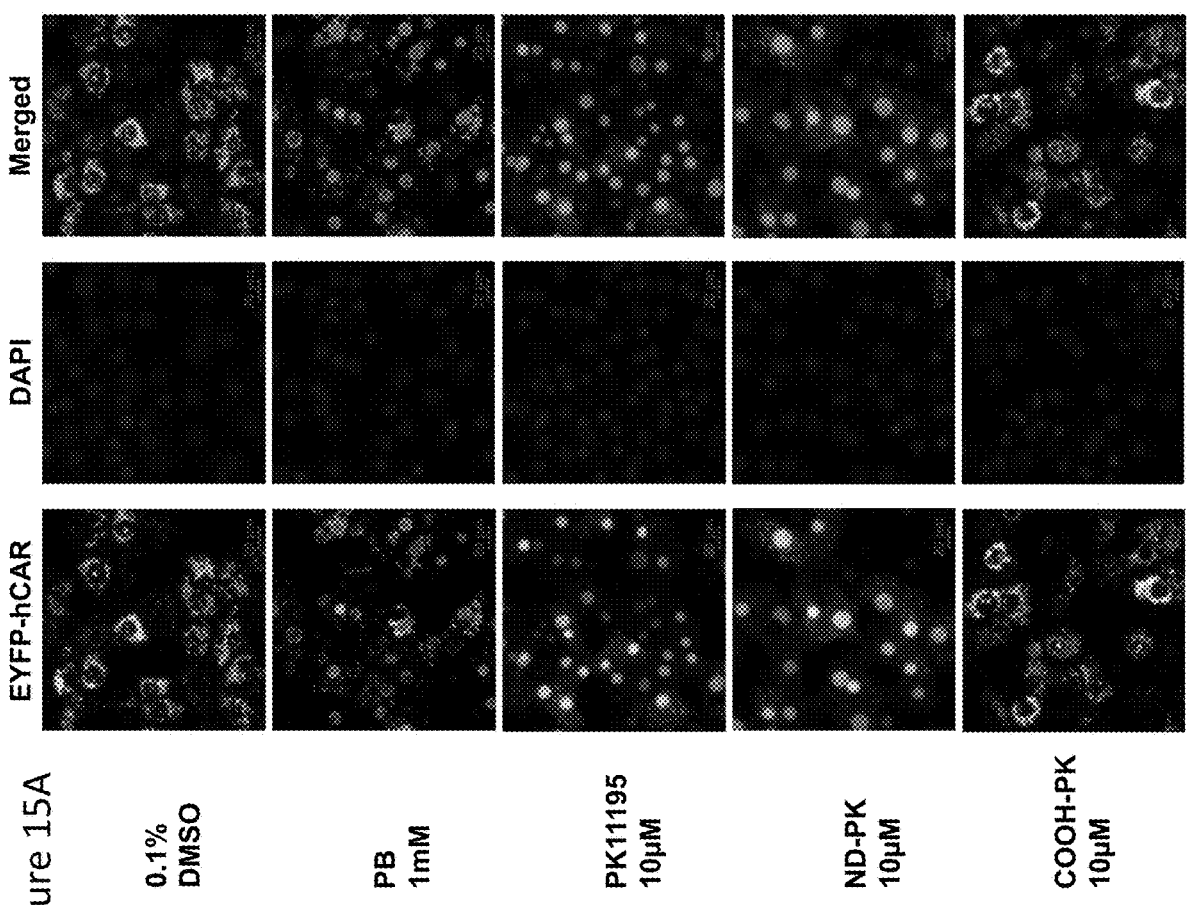
Figure 15A
Figure 15B

| | 1 | 2 | 3 | 4 | 5 | 6 | 7 | 8 | 9 | 10 | 11 | 12 |
|---|---|---|---|---|---|---|---|---|---|---|---|---|
| A | Insert TERF | Insert TERF | Insert TERF | CT TERF | CT TERF | CT TERF | IC TERF | IC TERF | | | | |
| B | Insert PHEN | Insert PHEN | Insert PHEN | CT PHEN | CT PHEN | CT PHEN | IC PHEN | IC PHEN | | | | |
| C | Insert BUP | Insert BUP | Insert BUP | CT BUP | CT BUP | CT BUP | IC BUP | IC BUP | | | | |
| D | Insert CHLZ | Insert CHLZ | Insert CHLZ | CT CHLZ | CT CHLZ | CT CHLZ | IC CHLZ | IC CHLZ | | | | |
| E | Insert 7-HC | Insert 7-HC | Insert 7-HC | CT 7-HC | CT 7-HC | CT 7-HC | IC 7-HC | IC 7-HC | | | | |
| F | | | | | | | | | | | | |
| G | | | | | | | | | | | | |
| H | | | | | | | | | | | | |

Figure 20

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: CYP2B6 primer sequence

<400> SEQUENCE: 1
agacgccttc aatcctgacc                                              20

<210> SEQ ID NO 2
<211> LENGTH: 21
<212> TYPE: DNA
<213> ORGANISM: Artificial Sequence
<220> FEATURE:
<223> OTHER INFORMATION: CYP2B6 primer sequence

<400> SEQUENCE: 2
ccttcaccaa gacaaatccg c                                            21

<210> SEQ ID NO 3
<211> LENGTH: 21
<212> TYPE: DNA
<213> ORGANISM: Artificial Sequence
<220> FEATURE:
<223> OTHER INFORMATION: CYP3A4 primer sequence

<400> SEQUENCE: 3
gtggggcttt tatgatggtc a                                            21
```

```
<210> SEQ ID NO 4
<211> LENGTH: 23
<212> TYPE: DNA
<213> ORGANISM: Artificial Sequence
<220> FEATURE:
<223> OTHER INFORMATION: CYP3A4 primer sequence

<400> SEQUENCE: 4
gcctcagatt tctcaccaac aca                                         23

<210> SEQ ID NO 5
<211> LENGTH: 21
<212> TYPE: DNA
<213> ORGANISM: Artificial Sequence
<220> FEATURE:
<223> OTHER INFORMATION: GAPDH primer sequence

<400> SEQUENCE: 5
cccatcacca tcttccagga g                                           21

<210> SEQ ID NO 6
<211> LENGTH: 21
<212> TYPE: DNA
<213> ORGANISM: Artificial Sequence
<220> FEATURE:
<223> OTHER INFORMATION: GAPDH primer sequence

<400> SEQUENCE: 6
gttgtcatgg atgaccttgg c                                           21
```

INVERTED CULTURE PLATE SYSTEM FOR CELLULAR CO-CULTURE

CROSS-REFERENCE TO RELATED APPLICATIONS

This application is the U.S. national phase application filed under 35 U.S.C. § 371 claiming benefit to International Patent Application No. PCT/US17/41054, filed Jul. 7, 2017, which is entitled to priority under 35 U.S.C. § 119(e) to U.S. Provisional Patent Application No. 62/359,367, filed Jul. 7, 2016, the contents of which are each incorporated by reference herein in their entirety.

STATEMENT REGARDING FEDERALLY SPONSORED RESEARCH OR DEVELOPMENT

This invention was made with government support under Grant Number GM107058 awarded by the National Institutes of Health. The government has certain rights in the invention.

BACKGROUND OF THE INVENTION

A shortcoming of currently used assays for screening drugs, environmental chemicals, and industrial compounds is that they do not consistently measure or otherwise assess metabolic competence. Many compounds are metabolically transformed in the body and if toxicity assays do not exhibit physiologically-relevant metabolism, they cannot accurately predict whether or not a compound will ultimately be toxic in humans.

One system that attempts to address metabolism in toxicity assays utilizes an insert that divides a cell culture well into two chambers, for example apical and basal chambers, with a permeable membrane in-between. However, there are many issues when using this model for simplistic co-culture. For example, certain cells have difficulty attaching to the permeable membranes. Further, in the context of high-throughput screening, most toxicity assays run in a 384- or 1536-well format, but the permeable membrane systems are commonly available only up to the 96-well format. Still further, the apical and basal chambers are designed to measure permeability, etc., but the membrane can inhibit the cell culture from sharing the media. Finally, using permeable membranes can be expensive, particularly for high-throughput uses.

There is a need in the art for an improved co-culture system. The present invention meets this need.

SUMMARY OF THE INVENTION

In one aspect, the present invention relates to a culture well insert. The culture well insert includes a planar substrate, at least one sidewall extending perpendicularly from the substrate to form an open top chamber within a perimeter of the at least one sidewall, and a well bottom surface positioned within the open top chamber of the at least one sidewall and between the open top of the chamber and the substrate. In one embodiment, the open top chamber has a cross-sectional shape selected from the group consisting of a circle, an oval, a square, a rectangle, a triangle, a pentagon, a hexagon, an octagon and an irregular shape. In another embodiment, the culture well insert includes at least one slit in the at least one sidewall extending from the open top of the chamber to the well bottom surface. In another embodiment, the culture well insert includes at least one aperture in the at least one sidewall positioned between the open top of the chamber and the well bottom surface. In another embodiment, the culture well insert includes at least one access port in the substrate, wherein the access port is adjacent the at least one sidewall. In another embodiment, the culture well insert includes at least one access port formed within a portion of the at least one sidewall. In another embodiment, the substrate further includes a raised lip along at least a portion of a perimeter of the substrate.

Also described is a culture well insert array. The array includes a planar substrate and a plurality of well inserts, each well insert including at least one sidewall extending perpendicularly from the substrate to form an open top chamber within a perimeter of the at least one sidewall, and a well bottom surface positioned within the open top chamber of the at least one sidewall and between the open top of the chamber and the substrate. In one embodiment, the open top chamber of each well insert has a cross-sectional shape selected from the group consisting of a circle, an oval, a square, a rectangle, a triangle, a pentagon, a hexagon, an octagon and an irregular shape. In another embodiment, each well insert further includes at least one slit in the at least one sidewall extending from the open top of the chamber to the well bottom surface.

In another embodiment, each well insert further includes at least one aperture in the at least one sidewall positioned between the open top of the chamber and the well bottom surface. In another embodiment, each well insert further includes at least one access port in the substrate, wherein each access port is adjacent the at least one sidewall of each well insert, respectively. In another embodiment, each well insert further includes at least one access port formed within a portion of the at least one sidewall of each well insert, respectively. In another embodiment, the substrate further includes a raised lip along at least a portion of a perimeter of the substrate.

Also described is a co-culturing system. The co-culturing system includes a receiving culture plate having at least one well, and a culture well insert array having at least one well insert, the culture well insert array including a planar substrate and at least one well insert, each well insert comprising at least one sidewall extending perpendicularly from the substrate to form an open top chamber within a perimeter of the at least one sidewall, and a well bottom surface positioned within the open top chamber of the at least one sidewall and between the open top of the chamber and the substrate. When the culture well insert array is inverted and positioned atop the receiving culture plate, the at least one well insert is sized to fit within the at least one well of the receiving culture plate such that the open top of the chamber of the at least one well insert does not contact the bottom of the at least one well of the receiving culture plate. In one embodiment, the open top chamber of the at least one well insert has a cross-sectional shape selected from the group consisting of a circle, an oval, a square, a rectangle, a triangle, a pentagon, a hexagon, an octagon and an irregular shape. In another embodiment, the at least one well insert further includes at least one slit in the at least one sidewall extending from the open top of the chamber to the well bottom surface. In another embodiment, the at least one well insert further includes at least one aperture in the at least one sidewall positioned between the open top of the chamber and the well bottom surface. In another embodiment, the at least one well insert further includes at least one access port in the substrate, wherein the access port is adjacent the at least one sidewall of the at least one well insert. In another embodiment, the at least one well insert further includes at least one access port formed within a portion of the at least one sidewall of the at least one well insert. In another embodiment, the substrate further includes a raised lip along at least a portion of a perimeter of the substrate.

Also described is a method of co-culturing a first population of cells with a second population of cells. The method includes the steps of culturing a first population of cells in a culture well insert having an open top well chamber, such that the first population of cells is adhered to at least a portion of the well chamber, culturing a second population of cells in a receiving well of a receiving culture plate, inverting the culture well insert, and inserting the inverted culture well insert into the receiving well of the receiving culture plate such that the open top of the chamber well insert does not contact the bottom of the receiving well of the receiving culture plate. In one embodiment, the method also includes the step of removing air bubbles from the open top well chamber of the culture well insert after insertion into the receiving well of the receiving culture plate. In another embodiment, the method includes the steps of adding, removing or exchanging culture media to the receiving well after insertion of the culture well insert into the receiving well of the receiving culture plate.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 3A and FIG. 3B depict exemplary inserts having an adjacent port (FIG. 3A) and a cutout port (FIG. 3B).

FIG. 5 depicts a cross-sectional side view of separate cell cultures in two exemplary well inserts (top) and two culture wells (bottom).

FIG. 9A through FIG. 9D depict the results of experiments demonstrating that PK11195 induces CYP2B6 and CYP3A4 expression in HPHs. Primary hepatocytes from liver donors 107 (FIG. 9A and FIG. 9B) and 122 (FIG. 9C and FIG. 9D) were treated with 1 mM PB, 1 µM CITCO, 10 µM RIF, or 10 µM PK11195 for 24 or 72 hours to analyze mRNA or protein expression, respectively. Results are expressed as fold over control, mean±S.D. (n=3); ***P <0.001.

FIG. 10A through FIG. 10D depict the results of experiments demonstrating that PK11195 induces CYP2B6 and CYP3A4 expression in HepaRG cells independent of PXR. Wild-type and PXR-KO HepaRG cells were cultured for 21 days in accordance with Sigma-Aldrich instructions to induce differentiation. Differentiated HepaRG cells were treated with 1 mM PB, 1 µM CITCO, 10 µM RIF, or 10 µM PK11195 for 24 or 72 hours to analyze mRNA (FIG. 10A and FIG. 10C) or protein expression (FIG. 10B and FIG. 10D), respectively. Data represent the mean±S.D. (n=3); n.s., not significant; *P<0.05; P<0.01; *P<0.001.

FIG. 14A through FIG. 14D depict the results of experiments demonstrating that ND-PK induces CAR target genes in HPHs. Primary hepatocytes from liver donors 120 (FIG. 14A and FIG. 14B) or 121 (FIG. 14C and FIG. 14D) were treated with PB (1 mM), CITCO (1 µM), RIF (10 µM), or increasing concentrations (0.1, 1, and 10 µM) of PK11195, ND-PK, or COOH-PK for 24 or 72 hours to analyze mRNA (FIG. 14A and FIG. 14C) or protein (FIG. 14B and FIG. 14D) expression, respectively. Data represent the mean±S.D. (n=3).

FIG. 15A and FIG. 15B depict the results of experiments demonstrating that ND-PK induces CAR nuclear translocation in HPHs. Primary hepatocytes from liver donor 123 were infected with adenovirus-expressing EYFP-hCAR for 24 hours and treated with 1 mM PB, 10 µM PK11195, 10 µM ND-PK, or 10 μM COOH-PK for 8 hours before being fixed with 4% paraformaldehyde, stained with 1 mg/ml 4',6-diamidino-2-phenylindole (DAPI), and visualized on a Nikon Eclipse TI fluorescent microscope. Quantitation of nuclear localization was determined using General Analysis in the Nikon Elements AR High Content Analysis software package and defined as the percentage of enhanced yellow fluorescent protein (YFP) that overlaps with DAPI. Representative images (FIG. 15A) and quantitative analysis (FIG. 15B) of nuclear localization are shown. Data represent the mean±S.D. of five individual images; $P<0.01$; *$P<0.001$.

FIG. 20 is schematic of a toxicology study setup on a standard 96-well plate.

DETAILED DESCRIPTION

Figure 1:
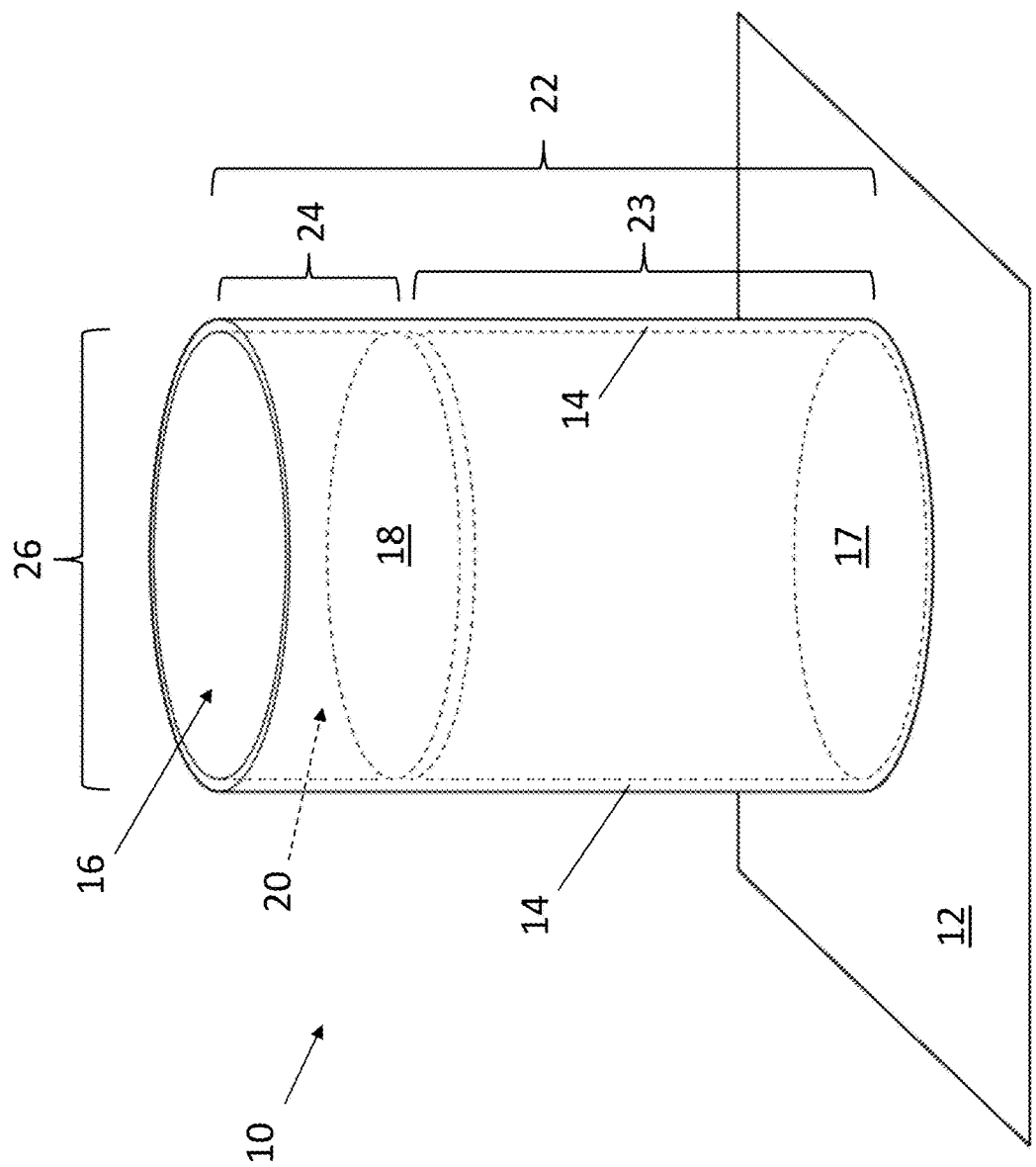
FIG. 1 depicts an isometric view of an exemplary well insert.

The present invention provides improved devices for co-culture of cells. The devices include inserts having invertible wells that can be lowered into a well of any standard cell culture plate. A first population of cells C can be cultured in the invertible wells of the inserts and a second population of cells C can be cultured in the wells of a cell culture plate. Once the first population of cells C attach to the invertible wells, the inserts are flipped over and placed into the wells of the cell culture plate to co-culture with the second population of cells C.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%,±5%,±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Culture Well Insert

The present invention provides well inserts for improved co-culture of cells C. The well inserts are adaptable and scalable to fit with any suitable single or multi-well cell culture plate, such as 6-well plates, 12-well plates, 24-well plates, 48-well plates, 96-well plates, 384-well plates, 1536-well plates, and the like. The well inserts are advantageous over membrane-based co-culture systems in several aspects. For example, the well inserts of the present invention can reliably hold an amount of cells C within the well, while other membrane-based co-culture systems must rely on surface tension of media to hold an amount of cells C on the outer side of an insert membrane. If the surface tension is broken in membrane-based co-culture systems, the cells will flow off of the membrane. The well inserts of the present invention are also able to culture a much wider variety of cells C, including cell lines that are otherwise difficult to adhere to permeable membranes. For example, the well inserts of the present invention are formed of non-permeable materials, such as polystyrene, which is generally cheaper than permeable materials, and facilitates cell plating.

Referring now to FIG. 1, an exemplary isolated well insert 10 is depicted. Well insert 10 generally includes a substrate or base member 12 from which at least one sidewall 14 extends perpendicularly towards an open top 16. Within a perimeter of sidewalls 14 is a well bottom 18, thereby forming a culture well 20 from well bottom 18, open top 16 and the portion of sidewalls 14 between well bottom 18 and open top 16. Well insert 10 further includes region 17, which in certain embodiments may be a closed surface contiguous with substrate 12, or region 17 may be a bottom opening into the perimeter of sidewalls 14.

The at least one sidewall 14 forms the three-dimensional hollow shell structure or perimeter boundary of culture well 20 of well insert 10. In the exemplary embodiment of FIG. 1, sidewall 14 is cylindrical and depicted to have a substantially circular cross-section. However, it should be appreciated that sidewalls 14 can have any suitable cross-sectional shape, including but not limited to elliptical, square, rectangular, triangular, pentagonal, hexagonal, octagonal, irregular, and the like. Sidewalls 14 can be constructed from any suitable material, including but not limited to plastic, polymer, rubber, glass, metal or combinations thereof. Sidewalls 14 may form a single unit with substrate 12, or sidewalls 14 may be separable from substrate 12.

Well bottom 18 may be a flat, planar surface or a curved surface, and may be perpendicular to sidewalls 14 or may alternatively be set at an angle that is more or less than 90° with respect to sidewalls 14. Further, well bottom 18 may be a smooth surface or it may be an irregular, textured surface. Well bottom 18 can be positioned at any suitable height along sidewalls 14, such that a position closer to open top 16 provides culture well 20 with a smaller volume, and a position closer substrate 12 provides culture well 20 with a larger volume. Well bottom 18 can be constructed from the same material or a different material as sidewalls 14. Well bottom 18 may form a single unit with sidewalls 14, or well bottom 18 may be a separate component from sidewalls 14 to allow well bottom 18 to be removable from, or adjustable within, sidewalls 14. Accordingly, in certain embodiments, the positioning of well bottom 18 within the perimeter of sidewalls 14 may be fixed, or it may be adjustable, such that a user can adjust the total volume of culture well 20. In still other embodiments, culture well 20 may have some or all of its surfaces of well bottom 18 and/or interior surfaces of sidewalls 14 functionalized with one or more molecules or material layers, such as cell adhesion coatings, specific binding molecules such as antibodies or other conjugates, and the like.

As described above, well insert 10 is adaptable and scalable to fit within any suitable single or multi-well cell culture plate. The dimensions of well insert 10 can be generally described by total height 22, well height 24, well displacement height 23 and width 26. Total height 22 is the total height of sidewalls 14 extending from substrate 12 to the rim of open top 16, and determines how deep well insert 10 reaches into the well of a cell culture plate when inserted. Total height 22 can be any suitable height, such as in the range between 5 and 50 mm, and will be dependent on the depth of the wells in the receiving culture plate. In certain embodiments, total height 22 is at least 5 mm, at least 10 mm, at least 15 mm, at least 20 mm, at least 25 mm, at least 30 mm, at least 35 mm, at least 40 mm, at least 45 mm or at least 50 mm. Well height 24 is the height of the portion of sidewalls 14 between well bottom 18 and the rim of open top 16. Well height 24 can be any suitable height, such as in the range between 1 and 10 mm. In certain embodiments, well height 24 is at least 1 mm, at least 2 mm, at least 3 mm, at least 4 mm, at least 5 mm, at least 6 mm, at least 7 mm, at least 8 mm, at least 9 mm or at least 10 mm. Generally, well height 24 is less than total height 22. Well displacement height 23 is the height of the portion of sidewalls 14 extending from substrate 12 to well bottom 18. Well displacement height can be any suitable height, such as in the range between 1 and 49 mm. In certain embodiments, well displacement height is at least 5 mm, at least 10 mm, at least 15 mm, at least 20 mm, at least 25 mm, at least 30 mm, at least 35 mm, at least 40 mm or at least 45 mm. In certain embodiments, displacement height 23 is greater than well height 24. In other embodiments, displacement height 23 is less than well height 24. Width 26 is the width of well insert 10, defined generally as the largest diameter of open top 16 within the perimeter of sidewalls 14. Width 26 can be any suitable width, such as in the range between 1 and 100 mm. Generally, width 26 will be less than the width or diameter of the well of the receiving culture plate to permit insertion of well insert 10 therein.

Figure 2:
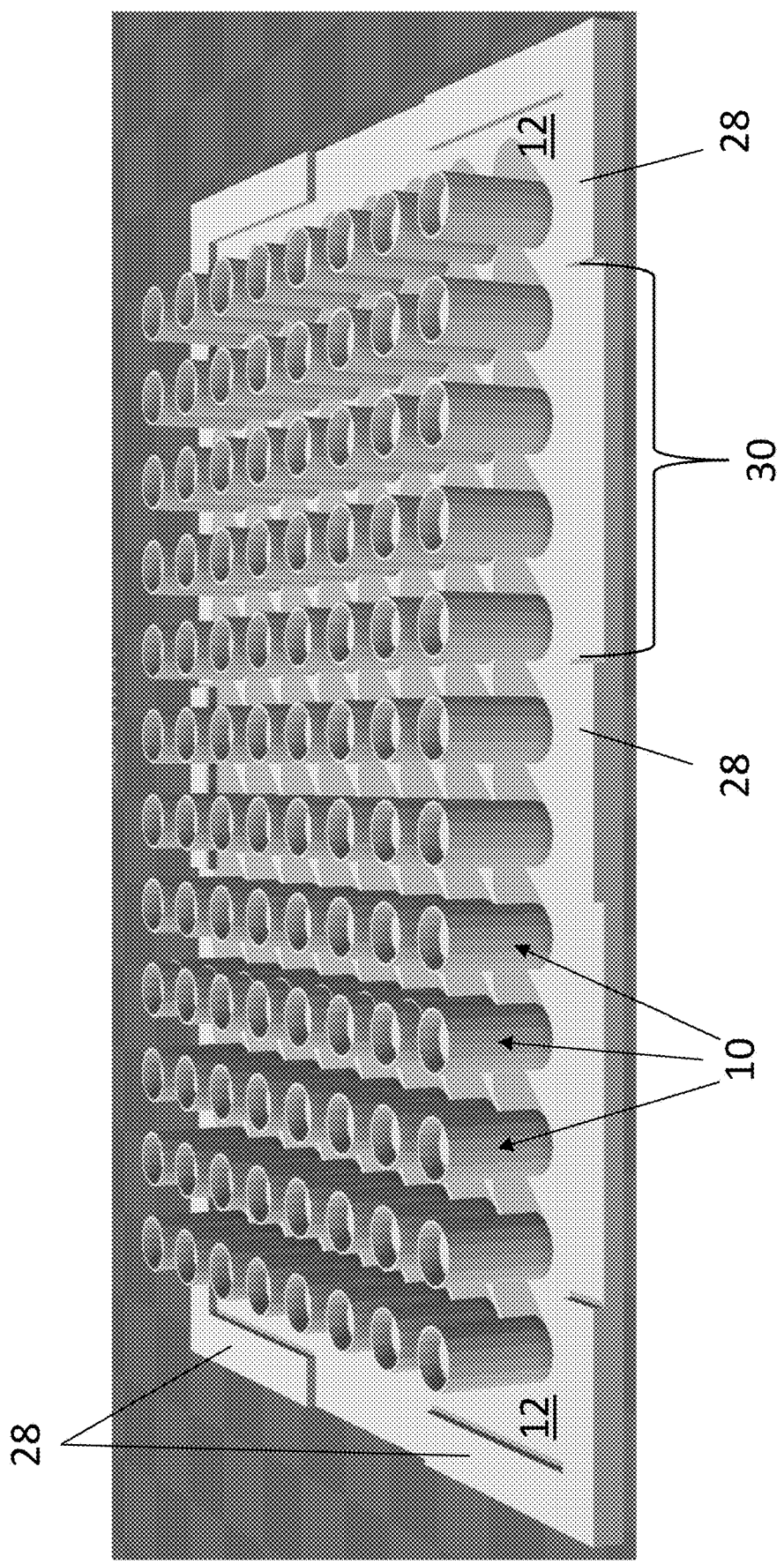
FIG. 2 depicts an exemplary 3D model of an array of well inserts adapted for use with a 96-well plate.

Referring now to FIGS. 1 and 2, one or more well inserts 10 can be attached onto a substrate 12, such as in an array matching the layout of a typical receiving multi-well cell culture plate. Substrate 12 may be a generally planar structure that secures each well insert 10 in place and can be constructed from any suitable material, such as plastic, polymer, rubber, glass, metal or combinations thereof. Substrate 12 may be generally rigid, or it may be flexible. In certain embodiments, substrate 12 comprises lip 28 along its perimeter. Lip 28 may have a height of 0.1 to 5 mm from the base surface of substrate 12, and may be segmented and capable of raising one or more sections 30 of substrate 12 off of the top of a receiving cell culture plate when positioned thereon, such that sections 30 provide gaps for airflow into each well of the receiving culture plate. In some embodiments, substrate 12 is a planar structure having an array of holes for inserting individual well inserts 10 (not illustrated). In such embodiments, each hole of the array on substrate 12 can be sized to friction fit or snap fit an individual well insert 10, such that an operator may determine and customize the number of well inserts 10 used, the pattern of well inserts 10 used, and the height of each well insert 10 used based on how far each well insert 10 is placed into each hole of the array.

In the exemplary embodiment of FIG. 2, an array of well inserts 10 are arranged on substrate 12 to mirror the size and spacing of a typical 96-well cell culture plate. To fit a typical 96-well cell culture plate, the particular embodiment in FIG. 2 comprises 96 well inserts 10 arranged in a grid having 8 rows and 12 columns, wherein each well insert 10 in each row and each well insert 10 in each column is spaced about 9 mm away from each other center-to-center. Lip 28 may have a thickness of 1 mm to provide a 1 mm gap between the base surface of substrate 12 and the top of a typical 96-well plate. Each well insert 10 comprises a height of about 11.17 mm, a width of about 5.85 mm, and a well height of about 2 mm to provide each insert culture well 20 a volume of about 50 μL.

Referring now to FIG. 3A, FIG. 3B, embodiments of substrate 12 having an access port are depicted. An access port provides an opening for airflow and also enables the introduction, removal, and/or sampling of media M or other substances without displacing or adjusting the position of substrate 12 when positioned on a receiving culture plate. Substrate 12 having access ports can be compatible with cell culture plates having wells that are wide enough to envelope both a well insert 10 and an access port. In FIG. 3A, an exemplary access port 32 is provided adjacent to well insert 10. In certain embodiments (not pictured), a substrate 12 having well insert 10 and access port 32 can be used with custom cell culture plates having irregularly sized wells that are capable of enveloping both well insert 10 and access port 32. In FIG. 3B, an exemplary access port 34 is provided with a modified well insert 10 such that the combined footprint of access port 34 and the modified well insert 10 is substantially equal to an unmodified well insert 10, thereby permitting access to the interior of the well of any standard receiving culture plate.

Figure 4B:
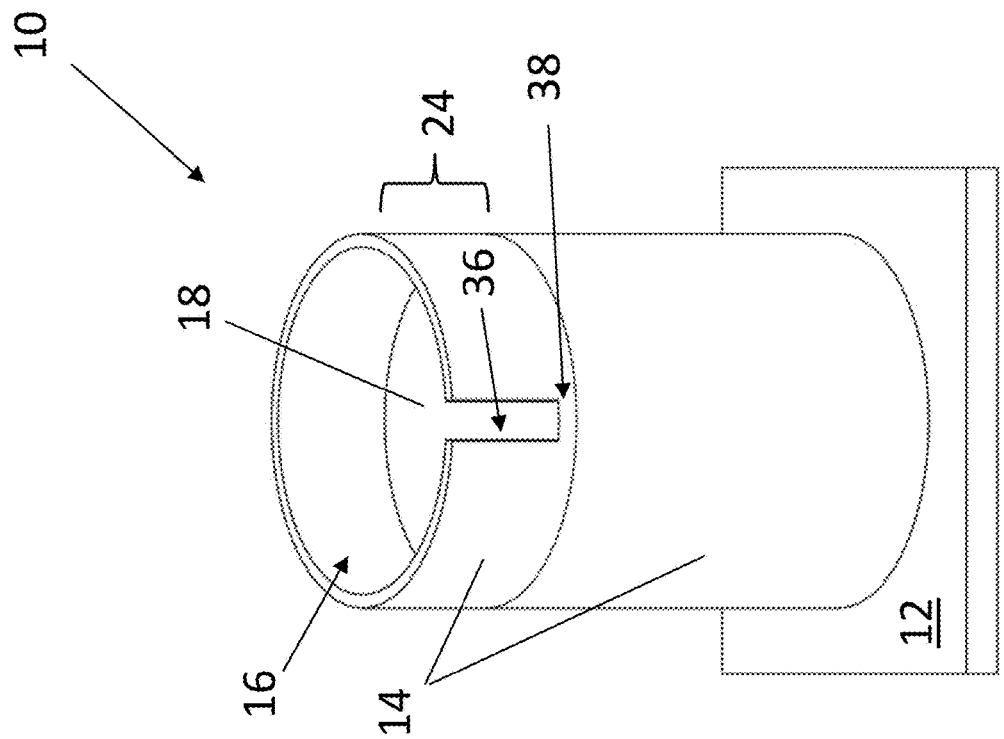
FIG. 4A and FIG. 4B depict an exemplary well insert having a slit.
Figure 4A:
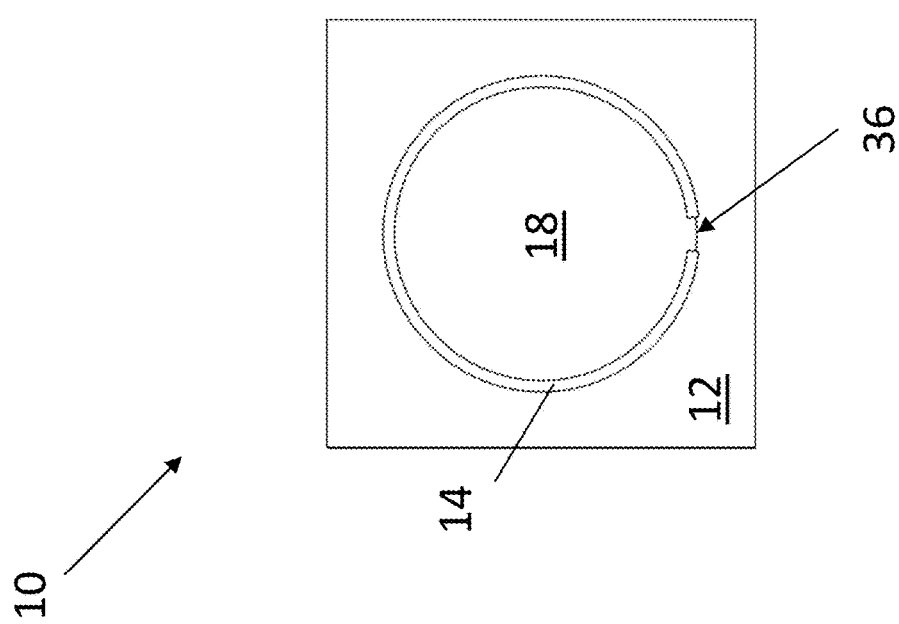

Referring now to FIG. 4, a top view (FIG. 4A) and an isometric view (FIG. 4B) of well insert 10 having at least one slit 36 are depicted. Slit 36 provides a space for air to escape out of insert culture well 20 when inverted and immersed in media M within the well of the receiving culture plate. Well insert 10 can include one or more slits 36 to accommodate greater volumes of air in larger insert culture wells 20. In some embodiments, slit 36 extends the entire well height 24. In other embodiments, slit 36 extends from the rim of open top 16 to a point that is less than the well height 24, thereby leaving a shortened sidewall region 38. In other embodiments, slit 36 may simply be an aperture or hole within sidewall 14, such as near the positioning of well bottom 18 within well height 24 (not shown). The width of slit or aperture 36 is small enough to utilize fluid surface tension to prevent fluid leakage out of well 20. In certain embodiments, slit or aperture 36 has a width of 0.1 to 2 mm. In still other embodiments, slit or aperture 36 may include a detachable portion of sidewall 14, such that the detachable portion may be in place and contiguous with the remainder of sidewall 14 while culturing cells C in culture well 20 prior to insertion into a receiving well culture, and then subsequently detached or otherwise removed to permit release of air bubbles when inserted into the receiving well.

The well inserts and substrates of the present invention can be made using any suitable method known in the art. The method of making may vary depending on the materials used. For example, devices substantially comprising a metal may be milled from a larger block of metal or may be cast from molten metal. Likewise, devices substantially comprising a plastic or polymer may be milled from a larger block or injection molded. In some embodiments, the devices may be constructed using 3D printing or other additive manufacturing techniques commonly used in the art.

Figure 6:
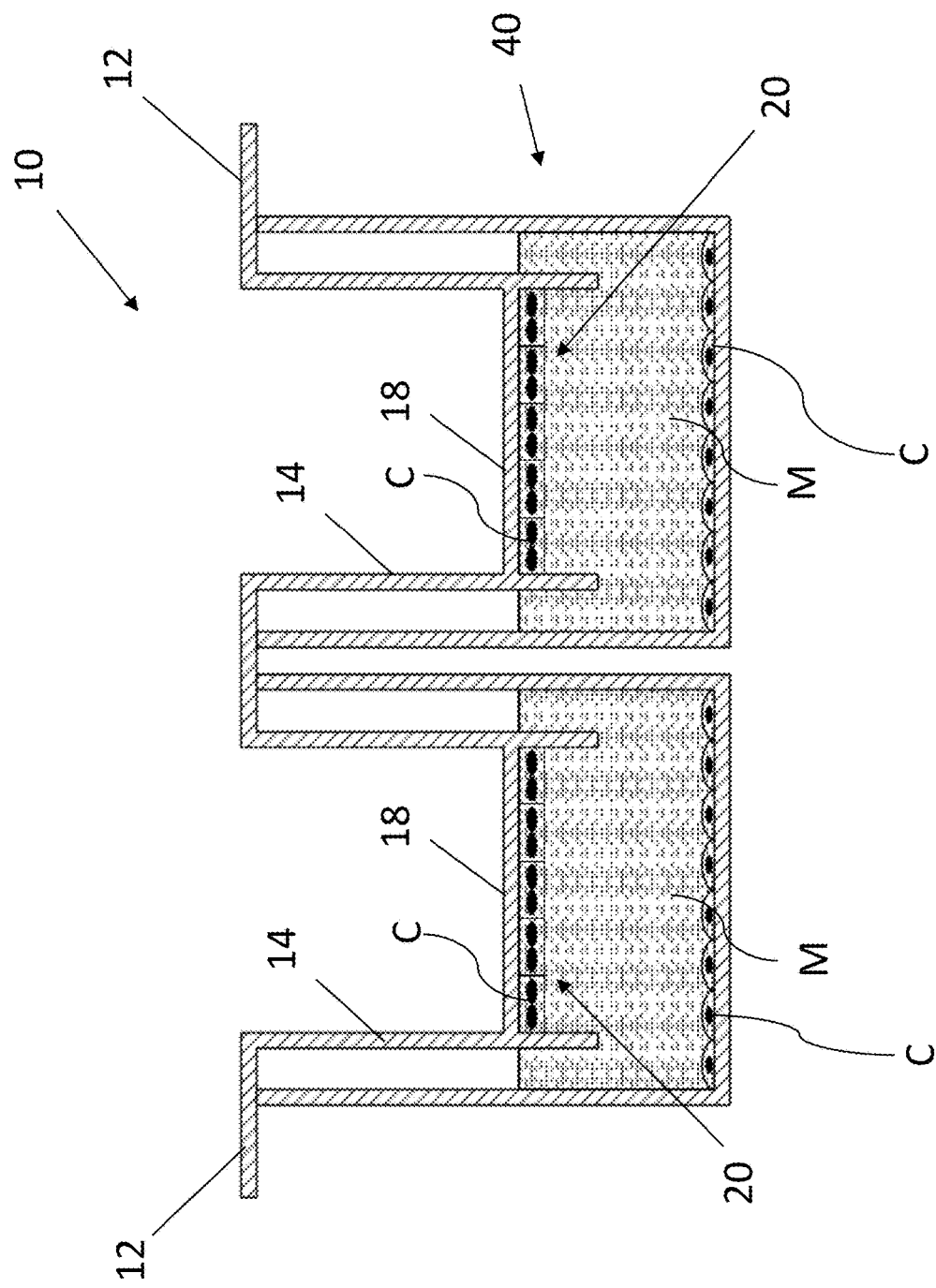
FIG. 6 depicts a cross-sectional side view of a co-culture between a first cell population adhered to two inverted exemplary well inserts and a second cell population adhered to two culture wells.
Figure 7:
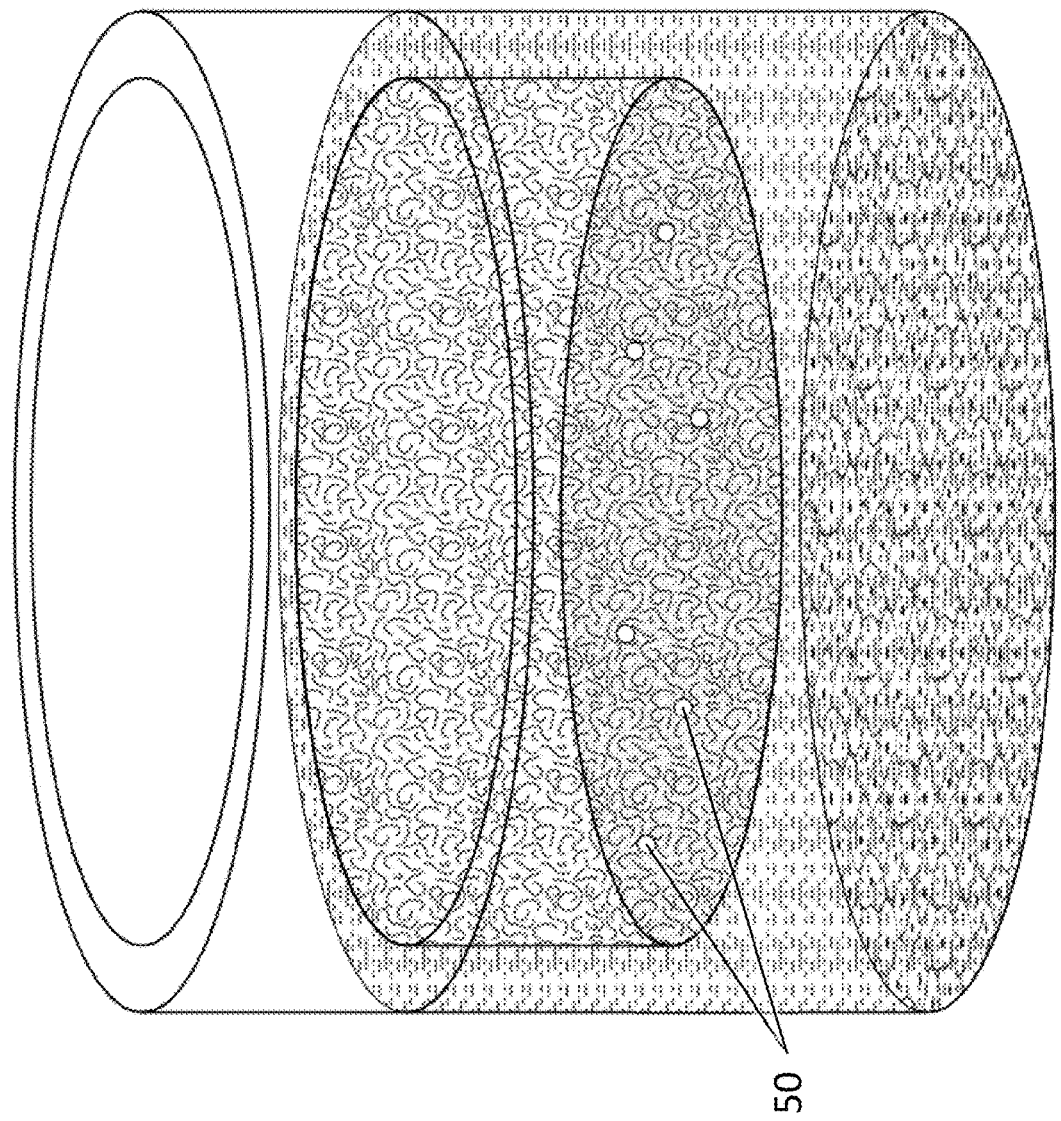
FIG. 7 depicts an isometric view of the shared volume of media between an inverted exemplary well insert and a culture plate well with free transfer of metabolites.

As described elsewhere herein, the well inserts of the present invention enable improved co-culture of cells C. Referring now to FIG. 5, FIG. 6, and FIG. 7, co-culturing cells C using the well inserts are depicted. In FIG. 5, a first population of cells C are cultured in insert culture wells 20 of two adjacent well inserts 10 (top) and a second population of cells C are cultured in two standard receiving culture wells 40 (bottom). The first population of cells C may be, without limitation, adherent cells C. Once the first population of cells C have adhered to well bottom 18, the well inserts 10 can be inverted and inserted into the receiving culture wells 40, as shown in FIG. 6. There is no limitation to the types of cells C used, and the first and second population of cells C may be the same cell types or different cell types. In other embodiments, more than two populations of cells may be used. The technique of inverting and inserting well inserts 10 can be performed in a variety of ways depending on the well inserts 10 and substrate 12 chosen. For example, well inserts 10 having at least one slit 36 can be inserted into a culture well 40 pre-filled with media M, whereupon air bubbles in well 20 evacuate through the at least one slit 36. In another example, well inserts 10 having at least one slit 36 can be inserted into a culture well 40 without media M, whereupon media M can be added to the culture well 40 through an access port 32 or 34 and air bubbles in well 20 evacuate as the media M level rises. In another example, well inserts 10 having smaller widths may be capable of holding a volume of media M due to fluid surface tension even when inverted, and can be simply inserted into a culture well 40 while holding the volume of media M. FIG. 7 depicts the shared volume of media M in a co-culture between an inverted well insert and a culture well with the free exchange of metabolites 50.

While FIG. 5, FIG. 6, and FIG. 7 each depict embodiments wherein a single well insert 10 is prepared and inserted into a single receiving culture well, it should be appreciated that more than one well insert 10 can be used in a co-culture with a single culture well. For example, multiple smaller well inserts 10 can be inserted into a larger culture well such that two, three, four, five, six, or more different cell populations adherent to each respective well insert can be co-cultured in a single, common receiving well.

Accordingly, the present invention may further include a co-culturing system, comprising any embodiments of the culture well inserts or arrays, and a corresponding receiving culture well plate as described herein. Such systems may additionally include one or more cell types and any type of culturing media M or other culturing additives desired. In one embodiment, a co-culturing system includes a receiving culture plate having at least one well, and a culture well insert array having at least one well insert or any sort as described herein. The culture well insert array can include a planar substrate and at least one well insert, each well insert including at least one sidewall extending perpendicularly from the substrate to form an open top chamber within a perimeter of the at least one sidewall, and a well bottom surface positioned within the open top chamber of the at least one sidewall and between the open top of the chamber and the substrate. In one embodiment, when the culture well insert array is configured to be inverted and positioned atop the receiving culture plate, the at least one well insert is sized to fit within the at least one well of the receiving culture plate such that the open top of the chamber of the at least one well insert does not contact the bottom of the at least one well of the receiving culture plate.

Components of the embodiments described herein can be included in a kit. For example, culture well inserts or arrays, and corresponding receiving culture well plate(s) can be packaged in one or more kits. Such kits may additionally include one or more cell types and/or media components. In certain embodiments, the kits are specific to one or more cell types or one or more type of culturing media. Kits may also include a variety of different sized or different geometry culture well inserts, arrays, and corresponding receiving culture well plates.

Figure 8:
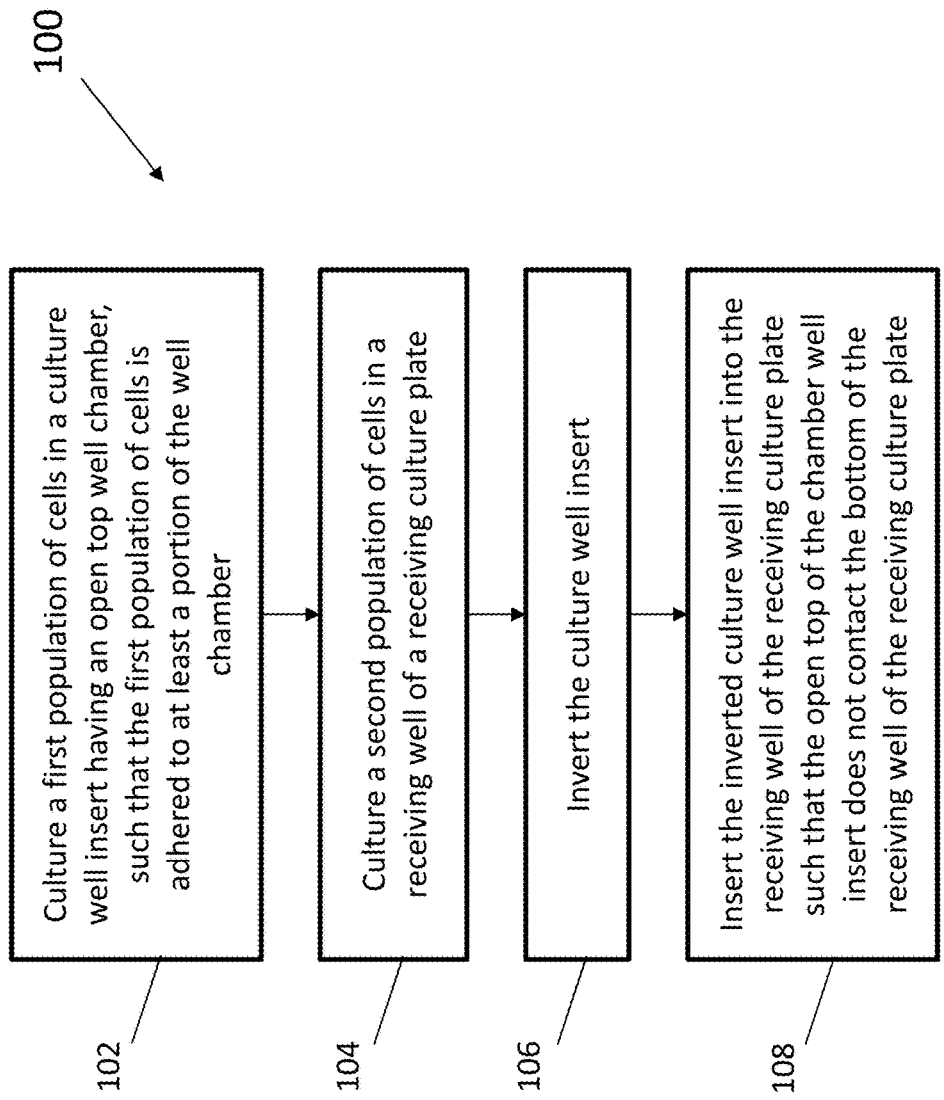
FIG. 8 depicts a flow chart of a method of co-culturing a first population of cells with a second population of cells according to one embodiment.

Further still, the present invention may include methods of co-culturing a first population of cells C with a second population of cells C using any of the embodiments of the culture well inserts, arrays and systems described herein. For example, the method may include the steps of culturing a first population of cells C in a culture well insert having an open top well chamber, such that the first population of cells C is adhered to at least a portion of the well chamber, culturing a second population of cells C in a receiving well of a receiving culture plate, inverting the culture well insert, and inserting the inverted culture well insert into the receiving well of the receiving culture plate such that the open top of the chamber well insert does not contact the bottom of the receiving well of the receiving culture plate. With reference specifically to FIG. 8, in one embodiment, a method 100 of co-culturing a first population of cells with a second population of cells is described. A first step includes culturing a population of cells in a culture well insert having an open top well chamber, such that the first population of cells is adhered to at least a portion of the well chamber 102. A second population of cells is cultured in a receiving well of a receiving culture plate 104. The culture well insert is inverted 106. Finally, the inverted culture well insert is inserted into the receiving well of the receiving culture plate such that the open top of the chamber well insert does not contact the bottom of the receiving well of the receiving culture plate 108. The method may further include the steps of removing air bubbles from the open top well chamber of the culture well insert after insertion into the receiving well of the receiving culture plate, as well as the steps of adding, removing or exchanging culture media M to the receiving well after insertion of the culture well insert into the receiving well of the receiving culture plate.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, utilize the present invention and practice the claimed methods. The following working examples therefore, specifically point out exemplary embodiments of the present invention, and are not to be construed as limiting in any way the remainder of the disclosure.

Example 1: Molecular Basis of Metabolism-Mediated Conversion of PK11195 from an Antagonist to an Agonist of the Constitutive Androstane Receptor The present study demonstrates that 1-(2-chlorophenyl)-N-methyl-N-(1-methylpropyl)-3-isoquinolinecarboxamide (PK11195) is N-demethylated to a metabolite that robustly activates constitutive androstane receptor (CAR) in human primary hepatocytes (HPHs). Using a human pregnane X receptor (PXR) knockout (KO) HepaRG cell line, PK11195 is confirmed to induce the expression of CYP2B6/CYP3A4 independent of PXR. A co-culture system of the present invention that adds metabolism to CAR luciferase reporter assays was used to determine how metabolism influences the agonist/antagonist feature of PK11195. Mammalian two-hybrid assays and molecular modeling were used to elucidate the molecular basis and structural features of PK11195 and its metabolites in the modulation of CAR activity.

The materials and methods are now described.

Chemicals and Biologic Reagents

Phenobarbital (PB), rifampicin (RIF), ketoconazole (KET), and PK11195 were obtained from Sigma-Aldrich (St. Louis, Mo.). 6-(4-Chlorophenyl)imidazo[2,1-b][1,3]thiazole-5-carbaldehyde-O-(3,4-dichlorobenzyl)oxime (CITCO) was obtained from BIOMOL Research Laboratories (Plymouth Meeting, Pa.). (R)-N-Desmethyl PK11195 (ND-PK) was obtained from ABX Advanced Biochemical Compounds (Radeberg, Germany). 1-(2-Chlorophenyl)isoquinoline-3-carboxylic acid (COOH-PK) was obtained from Biogene Organics (The Woodlands, Tex.). Polymerase chain reaction (PCR) primers were synthesized by Integrated DNA Technologies (Coralville, Iowa). HepaRG wild-type and PXR-KO cells and the cell culture medium were obtained from Sigma-Aldrich. Optima LC/MS Grade water ($H_2O$), acetonitrile (ACN), and formic acid were purchased from Fisher Scientific (Pittsburg, Pa.). All chemicals and reagents were used without further purification.

Culture and Treatment of HPHs and HepaRG Cells

HPHs were isolated using a modified two-step perfusion protocol (LeCluyse EL et al., (2005) Methods Mol Biol 290:207-229) from human liver specimens. The age and sex of each liver donor used are detailed in Table 1. Hepatocytes with viability over 90% were seeded at $0.75 \times 10^6$ cells/well in 12-well collagen-coated plates as described previously (Faucette SR et al., (2006) J Pharmacol Exp Ther 317:1200-1209). After attachment at 37° C. in a humidified atmosphere of 5% $CO_2$, hepatocytes were cultured in serum-free William's E Medium supplemented with insulin, transferrin, and selenium, 0.1 µM dexamethasone, 100 U/ml penicillin, and 100 µg/ml streptomycin, and overlaid with Matrigel (0.25 mg/ml). Thirty-six hours after seeding, HPHs were treated with vehicle control (0.1% [dimethylsulfoxide (DMSO)], CITCO (1 µM), RIF (10 µM), PB (1 mM), PK11195 (10 µM), ND-PK (10 µM), or COOH-PK (10 µM) for 24 or 72 hours before harvesting cells to collect RNA or protein, respectively. In separate experiments, wild-type and PXR-KO HepaRG cells were plated in 12-well plates ($1 \times 10^5$ cells/well) and cultured for 21 days following Sigma-Aldrich's instructions to induce differentiation before treatment with compounds as described previously.

Real-Time Reverse-Transcription PCR

Total RNA was isolated from cells using TRIzol reagent (ThermoFisher, Rockford, Ill.) and reverse transcribed using a High Capacity cDNA archive kit (Applied Biosystems, Foster, Calif.) according to the manufacturer's instructions. Real-time PCR assay was performed using SYBR Green PCR Mastermix (Qiagen, Germantown, Md.) on an ABI StepOnePlus real-timePCR system (Applied Biosystems). The primer sequences for CYP2B6, CYP3A4, and glyceraldehyde-3-phosphate dehydrogenase are as follows: CYP2B6, 5'-AGACGCCTTCAATCCTGACC-3' (SEQ ID NO: 1) and 5'-CCTTCACCAAGACAAATCCGC-3' (SEQ ID NO: 2); CYP3A4, 5'-GTGGGGCT-TTTAT-GATGGTCA-3' (SEQ ID NO: 3) and 5'-GCCTCAGAT-TTCTCACCAACACA-3' (SEQ ID NO: 4); and GAPDH, 5'-CCCATCACCATCTTCCAGGAG-3' (SEQ ID NO:5) and 5'-GTTGTCATGGATGACCTTGGC-3' (SEQ ID NO: 6). Expression values were quantified using the following equation: fold over control=$2^{\Delta\Delta Ct}$ method, where $\Delta Ct$ represents the differences in cycle threshold numbers between the target gene and glyceraldehyde-3-phosphate dehydrogenase, and $\Delta\Delta Ct$ represents the relative change in these differences between control and treatment groups.

Western Blot Analysis

Protein samples extracted from treated cells were electrophoretically separated on SDS-PAGE gels (4%-12%) and transferred to polyvinylidine fluoride membranes. Subsequently, membranes were incubated with primary antibodies against CYP2B6 (1:200; Santa Cruz Biotechnology, Santa Cruz, Calif.), CYP3A4 (1:5000; Sigma-Aldrich), or β-actin (1:50,000, Sigma-Aldrich) at 4° C. overnight. Blots were developed with West Pico chemiluminescent substrates (ThermoFisher) after incubation with horse-radish peroxidase secondary antibodies.

HepG2 Cell Transfection and HepG2/HPH Co-culture

Figure 11B:
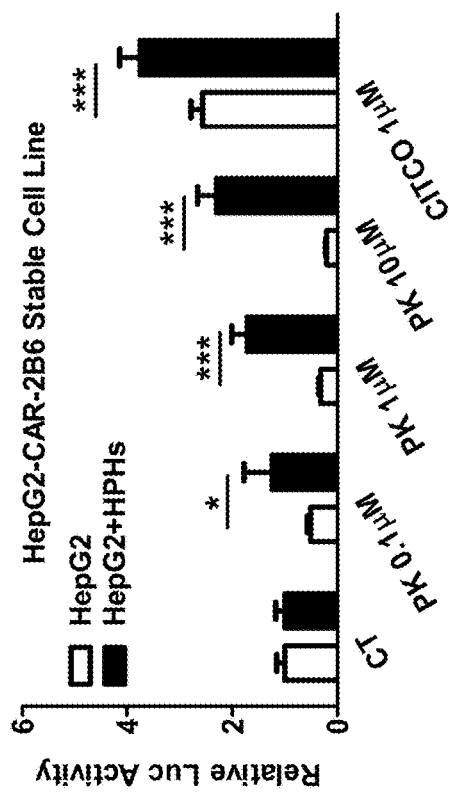
FIG. 11A through FIG. 11E depict the results of experiments demonstrating that PK11195 is metabolized to a CAR activator in HepG2-HPH co-culture. HPHs were plated on plastic cover slips with the corners bent upward and incubated with test compounds for 4 hours before the media and the coverslips were transferred to a 24-well plate containing HepG2 cells and incubated for 24 hours (FIG. 11A). HepG2-CAR-2B6 stable line (FIG. 11B) or transiently transfected with CAR1+A and CYP2B6-2.2K (FIG. 11C) were treated with PK11195 and CITCO at indicated concentrations with or without co-culture with HPHs for 24 hours. HepG2-CAR-2B6 cells alone (FIG. 11D) or co-cultured with HPHs (FIG. 11E) were treated with PK11195 alone or co-treated with 8 µM KET for 24 hours. Luciferase activity was measured as described in Experimental Example 1. Data represent the mean±S.D. (n=3); *P<0.05; ***P<0.001.
Figure 11C:
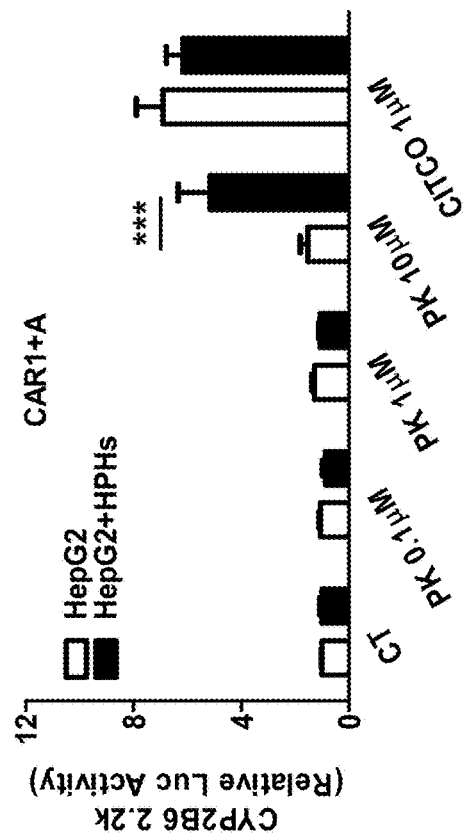

HepG2 or HepG2-CAR-CYP2B6 stable cells as described previously (Lynch C et al., (2015) Sci Rep 5:10405) were cultured in 24-well plates ($1\times10^5$ cells/well) at 37° C. and 5% $CO_2$ for 24 hours. HepG2 cells were co-transfected with CYP2B6-2.2k reporter (60 ng/well), hCAR1+A expression vector (30 ng/well), and pRL-TK (10 ng/well) by using X-tremeGENE 9 DNA Transfection Reagent (Sigma-Aldrich) following the manufacturer's instruction. Twenty-four hours after transfection, cells were treated with solvent (0.1% DMSO) or test compounds at indicated concentrations. Subsequently, cell lysates were assayed for firefly activities normalized against the activities of Renilla using a luciferase kit (Promega, Madison, Wis.). In separate experiments, HPHs were plated on collagen-coated cover slips with the corners bent upward in a 24-well plate. After preincubation of vehicle control and test compounds with HPHs for 4 hours, both the media and HPH-containing cover slips were transferred to new 24-well plates containing transfected HepG2 cells or the HepG2-CAR-2B6 stable line and incubated for 24 hours before measurement of luciferase activities. Data from a representative liver donor are shown in FIG. 11B and FIG. 11C and represent the mean±S.D. of three individual transfections.

Liquid Chromatography (LC)-Mass Spectrometry (MS) Measurement of PK11195 Metabolism Complete William's E Medium containing 10 mM PK11195 was added to HPHs cultured in 24-well plates 36 hours after seeding. Media (450 µl ) were collected from each well at 0 and 1 hours and frozen immediately at −80° C. Samples were thawed on ice before adding 50 µl of medium to 450 µl of ice-cold methanol/$H_2O$ (8:1, v/v). After centrifugation at 16,000g for 30 minutes, 200 µl of supernatant was transferred to a separate tube and dried down before resuspension in 200 µl $H_2O$/ACN (1:1, v/v) with 0.1% formic acid. Authentic standards were prepared to 1 µM in $H_2O$/ACN (1:1, v/v) with 0.1% formic acid. LC-MS/MS analysis was performed on a TSQ Quantum Ultra Triple Stage Quadrupole Mass Spectrometer coupled to an Ultimate 3000 RS Liquid Chromatogram System (Thermo Scientific, Waltham, Mass.). The LC separation was performed on a Waters (Milford, Mass.) BEH C18 column (2.1×50 mm, 1.7 µm) operated at 30° C. Solvents A and B consisted of 0.1% formic acid in $H_2O$ and 0.1% formic acid in ACN, respectively. The gradient program was 0.0-0.5 minutes, 50% B; 0.5-2.0 minutes, gradient to 95% B; 2.0-3.5 minutes, 95% B; 3.5-4.0 minutes, gradient to 50% B; and 4.0-5.0 minutes, 50% B. The flow rate was 0.5 ml/min and injection volume was 5 µl. Tandem mass spectrometry was performed in the positive-ion mode and the electrospray ionization source parameters were as follows: spray voltage, 3000; capillary temperature, 325; sheath gas pressure, 40; auxiliary gas pressure, 15; capillary offset, 35; and tube lens offset, 80. Selected reaction monitoring was used for mass detection with the following transitions: PK11195 (m/z 353.1→238.0), ND-PK (m/z 339.1→238.0), and COOH-PK (m/z 284.0→238.0). Data collection and analysis were performed using Xcalibur V 2.1 (Thermo Scientific).

Mammalian Two-Hybrid Assay

COS1 cells seeded in 24-well plates were transfected with 110 ng of the reporter gene plasmid pG5luc, 80 ng of expression plasmids encoding the respective VP16AD/hCAR fusions, 40 ng of expression plasmids encoding GAL4-DBD/coregulatory fusions, and 20 ng of reference plasmid pRL-TK, each well using X-tremeGENE 9 DNA Transfection Reagent (Sigma-Aldrich). Twenty-four hours after transfection, the cells were treated with solvent (0.1% DMSO), CITCO (1 µM), PK11195 (10 µM), or ND-PK (10 µM) for 24 hours. Luciferase activities were measured in cell lysates using the Dual Luciferase Kit (Promega). Data represent the mean±S.D. of three individual transfections.

Nuclear Translocation of CAR in HPHs

HPHs were plated in collagen-coated 24-well plates and infected with adenovirus-expressing enhanced yellow fluorescent protein-tagged hCAR (EYFP-hCAR) as described previously (Li H et al., (2009) Drug Metab Dispos 37:1098-1106). Twenty-four hours after infection, HPHs were treated with vehicle control (0.1% DMSO), PB (1 mM), PK11195 (10 µM), ND-PK (10 µM), or COOH-PK (10 µM) for another 8 hours. After treatment, cells were fixed with 4% paraformaldehyde, stained with 1 µg/ml 4',6-diamidino-2-phenylindole (Sigma-Aldrich) for 30 minutes, and EYFP-hCAR localization in hepatocytes was visualized on a Nikon Eclipse TI fluorescent microscope (Nikon, Melville, N.Y.). Quantitative distribution of EYFP-hCAR was analyzed using General Analysis in the Nikon Elements AR High Content Analysis software package (version 4.50.00). Nuclear localization was defined and quantified as the percentage of total enhanced yellow fluorescent protein that overlaps with 4',6-diamidino-2-phenylindole. Data from a representative liver donor are shown in FIG. 15A and FIG. 15B and represent the mean±S.D. of five individual images for each treatment.

Molecular Modeling

The hCAR/ligand-binding domain protein crystal structure (Protein Data Bank identification number 1XVP) was retrieved from the RCSB Protein Data Bank (http://www.rcsb. org). The PK11195 and ND-PK molecular structures were generated and obtained from ChemAxon Chemicalize (http://chemicalize.com) and the CITCO and CAR inhibitor not PXR activator 1 (CINPA1) structures were obtained from National Center for Biotechnology Information PubChem (http://pubchem.ncbi.nlm.nih.gov/). Discovery Studio (version 4.5.0.15071; Biovia, San Diego, Calif.) was used to remove water and ligands from the crystallographic data and isolate the D chain protein that contains the crystal structure of CAR, which was subsequently protonated at pH 7.0. binding site was defined based on the CITCO binding cavity and defined as an 11.5 Å radius sphere at 24.972 (x), 54.702 (y), and 29.512 (z). The receptor-ligand docking was performed in Discovery Studio using the CDOCKER protocol (Wu G et al., (2003) J Comput Chem 24:1549-1562). Briefly, the docking parameters were set to generate 255 conformations for each ligand and return the top 10 docks with the lowest CDOCKER energy, which is the sum of the receptor ligand interaction energy and internal ligand strain. The ligand-receptor interactions of the docked molecules were analyzed and visualized in Discovery Studio.

Statistical Analysis

All data are expressed as the mean±6 S.D. Statistical comparisons were made using one-way analysis of variance with Dunnett's post-test or two-way analysis of variance with Bonferroni post-test as needed. Statistical significance was set at *$P<0.05$, $P<0.01$, and *$P<0.001$.

The results are now described.

PK11195 Induces the Expression of CYP2B6 and CYP3A4 in HPHs

The effects of PK11195, a known hCAR antagonist, was first examined on the expression of CYP2B6 and CYP3A4, two prototypical targets for hCAR and hPXR, in HPHs prepared from liver donors 107 and 122. As shown in FIG. 9A through FIG. 9D, PB, CITCO, RIF, and PK11195 at selected concentrations robustly induced CYP2B6 and CYP3A4 at mRNA and protein levels in both liver donors. As expected, CITCO (a selective activator of hCAR) and RIF (a selective activator of hPXR) preferentially induced the expression of CYP2B6 and CYP3A4, respectively. Intriguingly, PK11195 at 10 μM, a concentration at which it represses the activity of hCAR by more than 85% in HepG2 cells (Li L et al., (2008) Mol Pharmacol 74:443-453), markedly induced the expression of both CYP2B6 and CYP3A4 without a clear preference, mimicking PB, a dual activator of hCAR and hPXR. These findings call into question whether PK11195 is an antagonist of hCAR in physiologically relevant cells and challenge the assumption that PK11195 induction of cytochrome P450 (P450) in HPHs relies on PXR activation.

Induction of CYP2B6 and CYP3A4 by PK11195 in PXR-KO HepaRG Cells

HepaRG cells have been validated as a promising surrogate for HPHs, and importantly, fully differentiated HepaRG cells exhibit proper CAR cellular localization and maintain physiologically relevant metabolic capacity, which are not present in most immortalized cell models (Jackson JP et al., (2016) Drug Metab Dispos 44:1463-1479). The PXR-KO HepaRG cell line obtained from Sigma-Aldrich is a newly generated cell line that does not express functional PXR (Williamson B et al., (2016) Pharmacol Res Perspect 4:e00264). As expected, PK11195 and other known CAR/PXR modulators induced the expression of CYP2B6 and CYP3A4 mRNA and protein in wild-type HepaRG cells in a trend that mirrors what was observed in HPHs (FIG. 10A and FIG. 10B). Notably, in PXR-KO HepaRG cells PK11195 significantly induced both CYP2B6 and 3A4 expression at mRNA and protein levels, although induction of CYP2B6 and CYP3A4 by RIF was fully abrogated (FIG. 10C and FIG. 10D). These data suggest that differential metabolism of PK11195 in the physiologically relevant HPH/HepaRG cells versus the immortalized HepG2 cells may contribute to the observed PXR-independent induction of CYP2B6 and CYP3A4.

PK11195 is Metabolized to a hCAR Activator in HPHs

Figure 11A:
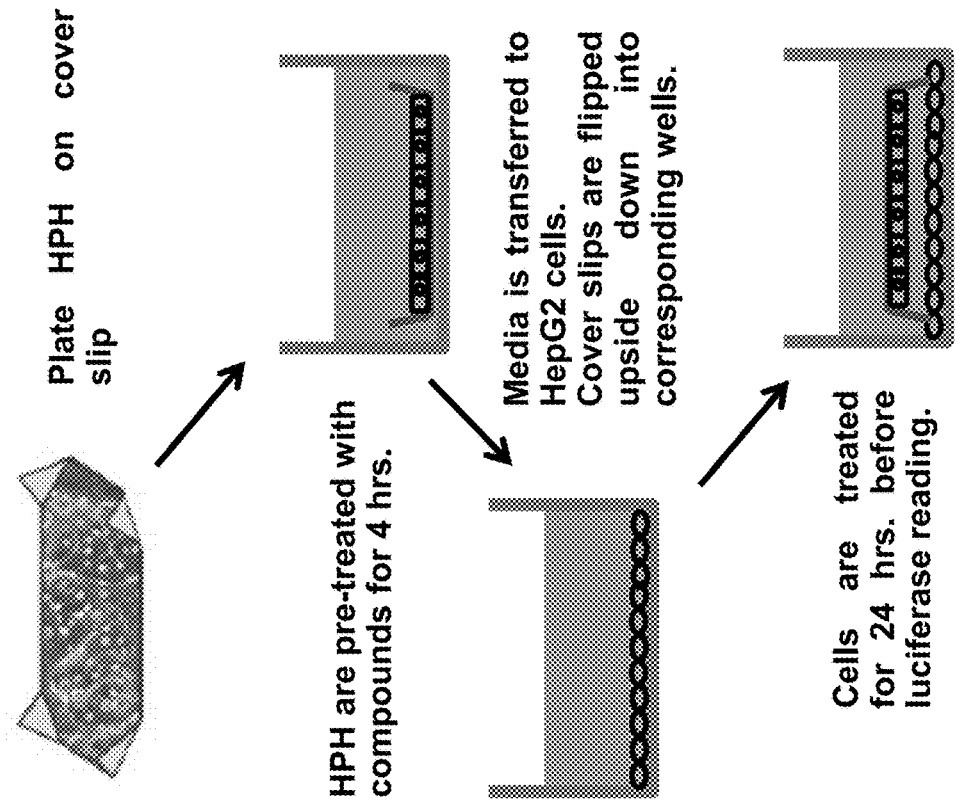
Figure 11E:
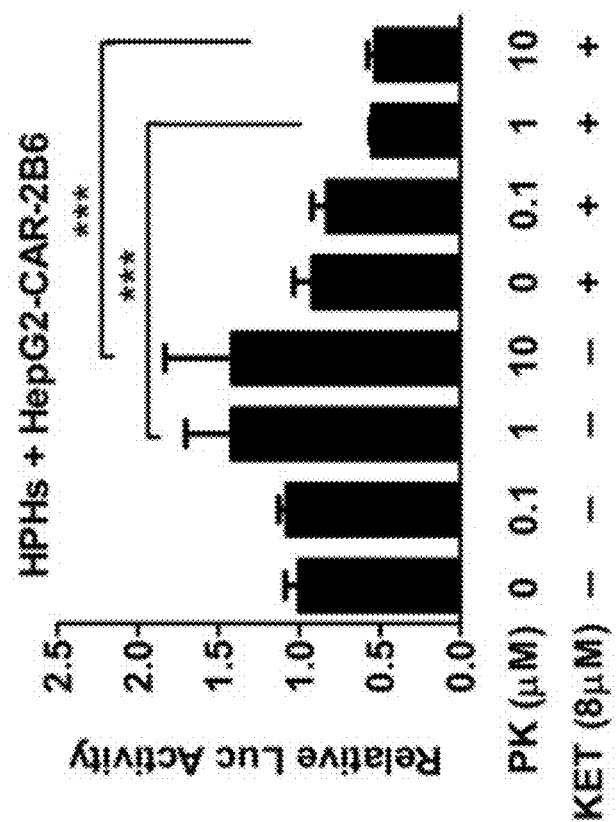
Figure 11D:
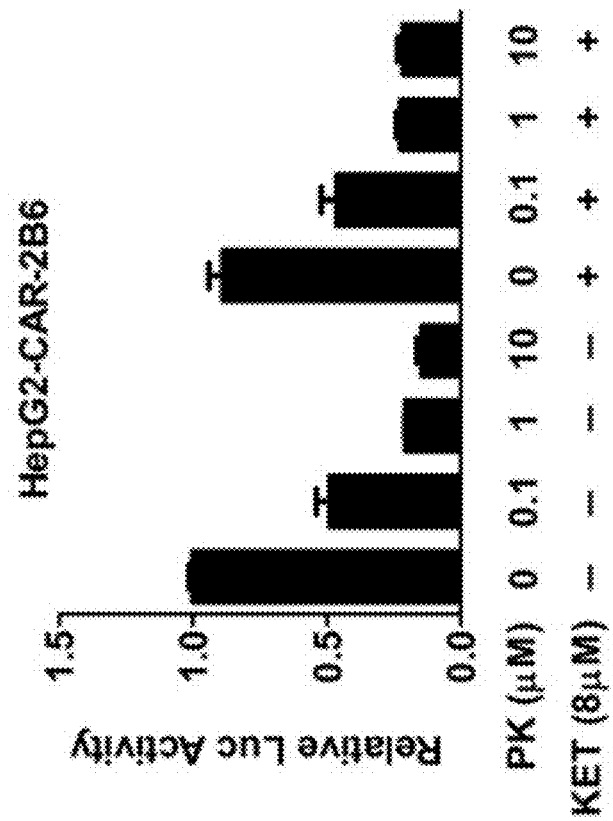

Lack of metabolism is a major limitation of almost all studies using immortalized cell lines, including HepG2 cells. A HPH-HepG2 co-culture model was established as depicted in FIG. 11A, which introduces the metabolism-competent HPHs into the culture environment shared with HepG2 cells. In agreement with previous reports, PK11195 concentration dependently inhibits the constitutive hCAR activity in HepG2 cells without the presence of HPHs (FIG. 11B, open bars). Results from the co-culture with HPHs from a representative liver donor indicate that PK11195 significantly increased the luciferase activity of the CYP2B6 reporter in the presence of hCAR (FIG. 11B, solid bars) or its low-basal alternative hCAR11A (FIG. 11C). These findings suggest that PK11195 is converted from a CAR antagonist to an agonist in the presence of HPHs. To further explore the contribution of metabolism in this antagonism/agonism conversion, KET, a potent inhibitor of CYP3A4, the most abundant hepatic P450 isoform in humans, was co-treated with different concentrations of PK11195 in HepG2-CAR-2B6 cells with and without HPH co-culture. Repression of CAR activity by PK11195 was not influenced by the presence of KET in HepG2-CAR-2B6 cells alone (FIG. 11D). On the other hand, when HPHs were co-cultured with HepG2-CAR-2B6 cells, KET significantly inhibited the conversion of PK11195 (1 and 10 μM) from a CAR antagonist to a CAR activator (FIG. 11E). Taken together, these results validate the use of the co-culture system to investigate the mechanistic effects of metabolism on CAR activity and suggest that CYP3A4 contributes to the biotransformation of PK11195 in HPHs.

PK11195 Is Metabolized to ND-PK and COOH-PK in HPHs

Figure 12B:
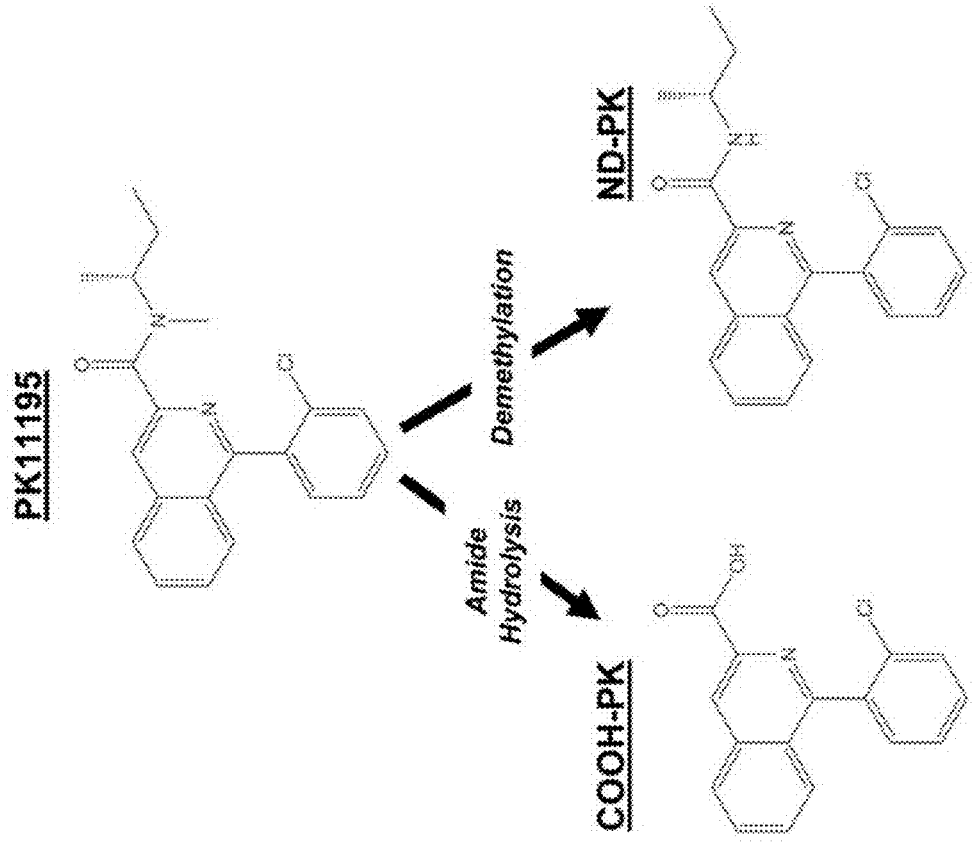
FIG. 12A through FIG. 12D depict the results of experiments demonstrating that PK11195 is metabolized to COOH-PK and ND-PK in HPHs. Proposed PK11195 metabolism pathway (FIG. 12A). An authentic 1 µM standard mix was run on LC-MS/MS as described in Experimental Example 1 and retention times for PK11195, COOH-PK, and ND-PK were determined to be 1.81, 0.76, and 2.14, respectively (FIG. 12B). Media containing 10 µM PK11195 was cultured with HPHs and harvested at 0 hour (FIG. 12C) and 1 hour (FIG. 12D) to determine whether PK11195 is metabolized by HPHs to the metabolites of interest.
Figure 12A:
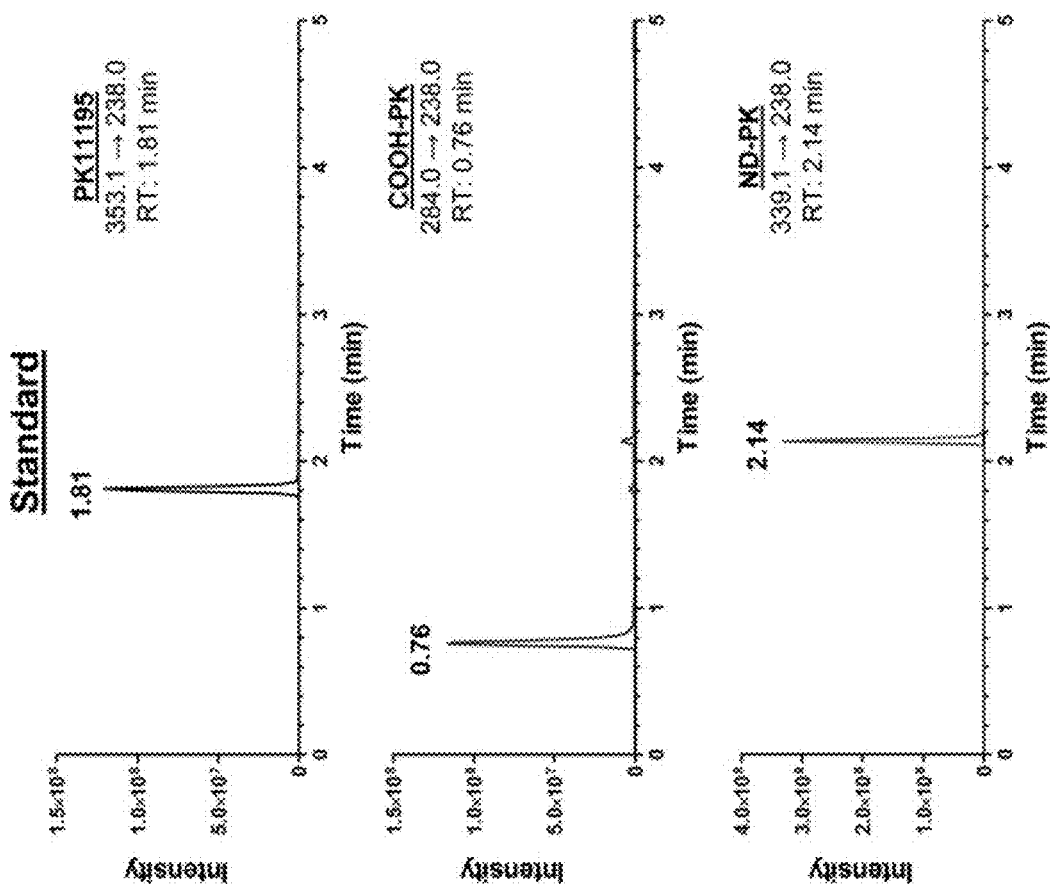
Figure 12C:
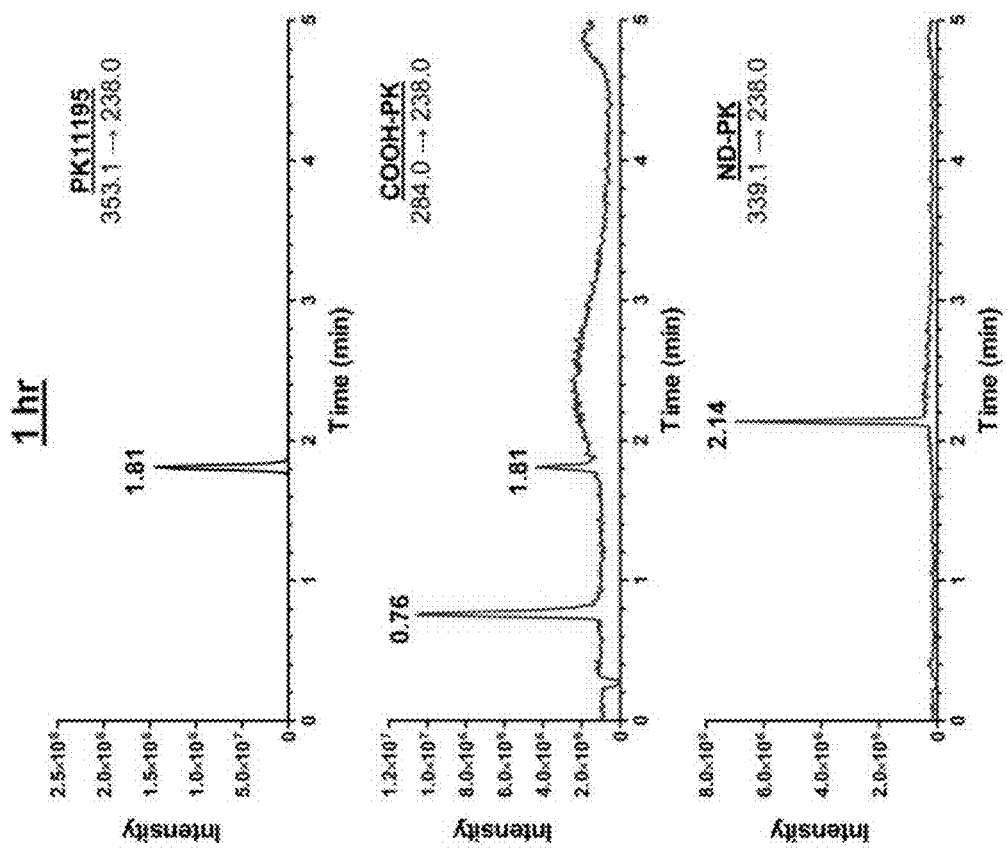
Figure 12D:
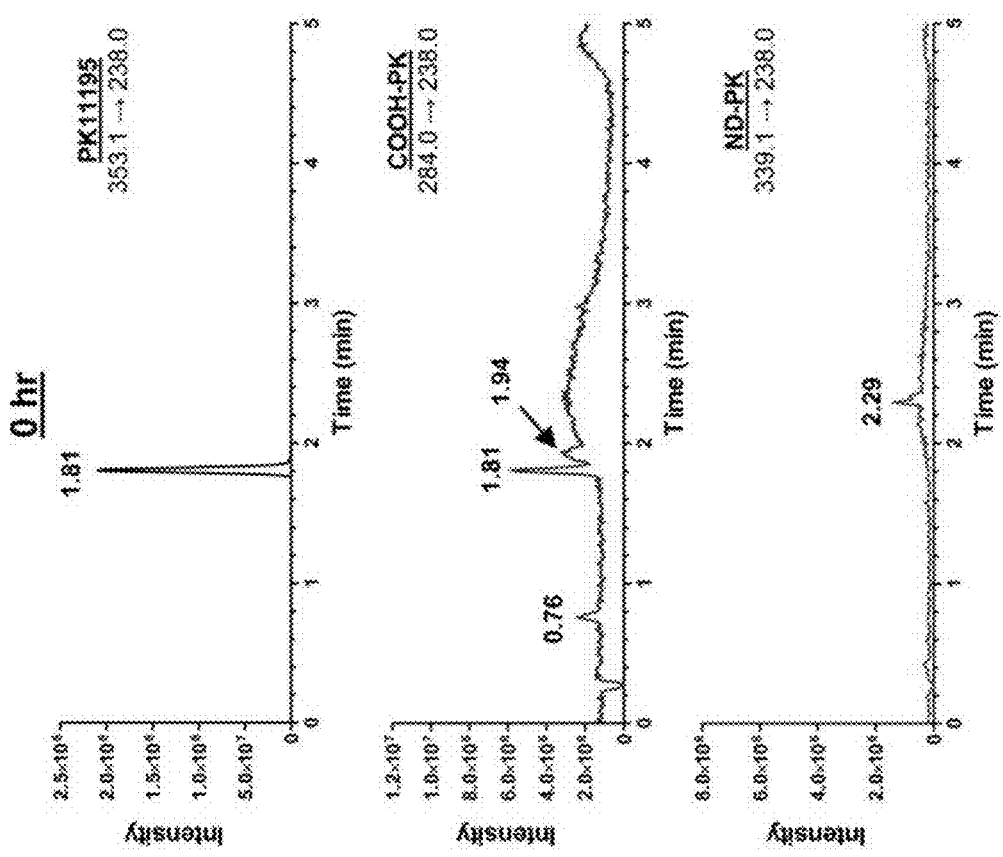

Previous studies postulated that PK11195 is metabolized into two major metabolites, ND-PK and COOH-PK, which are formed through N-demethylation and amide hydrolysis, respectively (FIG. 12A) (Roivainen A et al., (2009) Eur J Nucl Med Mol Imaging 36:671-682). To confirm that these metabolites were generated in the experimental system, PK11195 (10 μM) was incubated with HPHs and media was collected at 0 and 1 hours. These samples were prepared and analyzed by LC-MS/MS as detailed in the methods and materials to determine whether the proposed ND-PK and COOH-PK metabolites of PK11195 were formed in HPHs. The 1 μM standard mix exhibited chromatographic separation and reproducible retention times of 1.81, 0.76, and 2.14 for PK11195, COOH-PK, and ND-PK, respectively (FIG. 12B). As expected, PK11195 was abundantly present in HPH culture medium at 0 hour, while the amounts of COOH-PK and ND-PK were negligible (FIG. 12C). However, the peaks for COOH-PK and ND-PK significantly increased in intensity after 1 hour in HPH culture, indicating that PK11195 is metabolized by HPHs to COOH-PK and ND-PK FIG. 12D). This is the first report confirming that the COOH-PK and ND-PK metabolites of PK11195 are generated by HPHs.

The (R)-N-Desmethyl Metabolite of PK11195 Mediates hCAR Activation

Figure 13B:
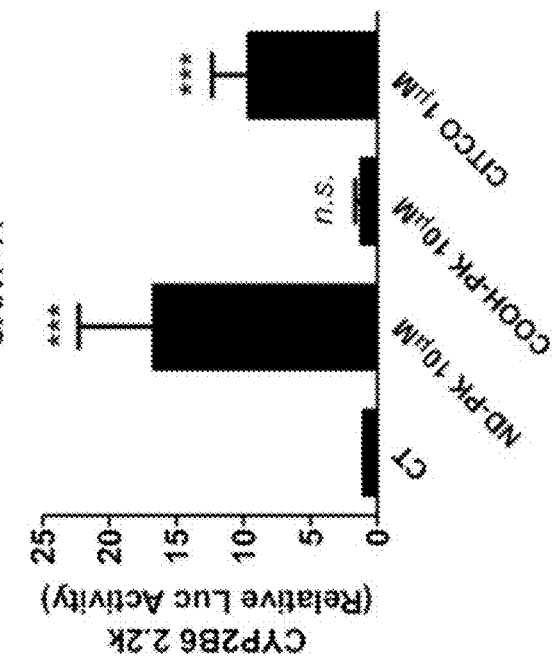
FIG. 13A through FIG. 13F depict the results of experiments demonstrating that the (R)-N-desmethyl (ND) metabolite of PK11195 mediates CAR activation. HepG2-CAR-2B6 cells (FIG. 13A) and HepG2 cells transfected with CAR1+A and CYP2B6-2.2k (FIG. 13B) were treated with vehicle control (CT), ND-PK, COOH PK, or CITCO at indicated concentrations for 24 hours before luciferase activities were determined. Mammalian two-hybrid assays were performed in COS1 cells measuring interaction between CAR/SRC-1 (FIG. 13C) or CAR/ GRIP1 (FIG. 13D) as detailed in Experimental Example 1. Transfected cells were treated with CITCO, PK11195, ND-K, or ND-PK+PK11195 for 24 hours before determining luciferase activity. PXR-KO HepaRG cells were treated with vehicle control, PB (1 mM), CITCO (1 µM), RIF (10 µM), ND-PK (10 µM), or COOH-PK(10 µM) and harvested for mRNA (FIG. 13E) or protein (FIG. 13F) expression analysis. Data represent the mean±S.D. (n=3); n.s., not significant; *P<0.05; P<0.01; *P<0.001.
Figure 13A:
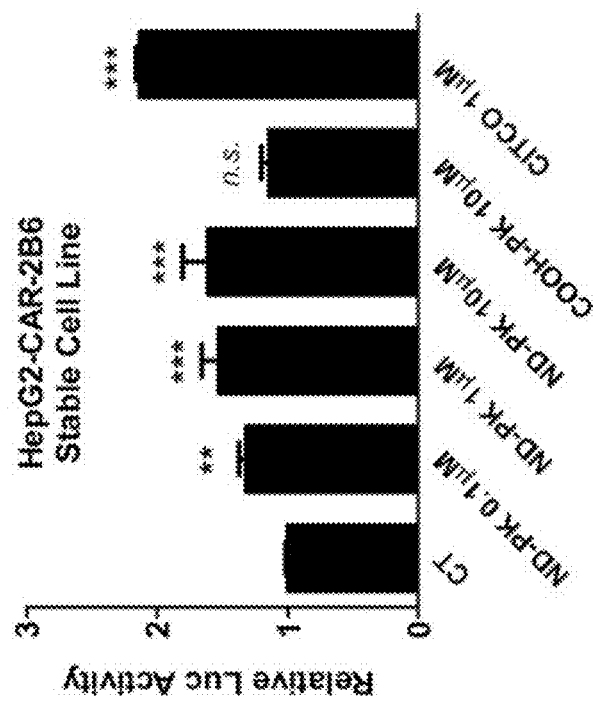
Figure 13D:
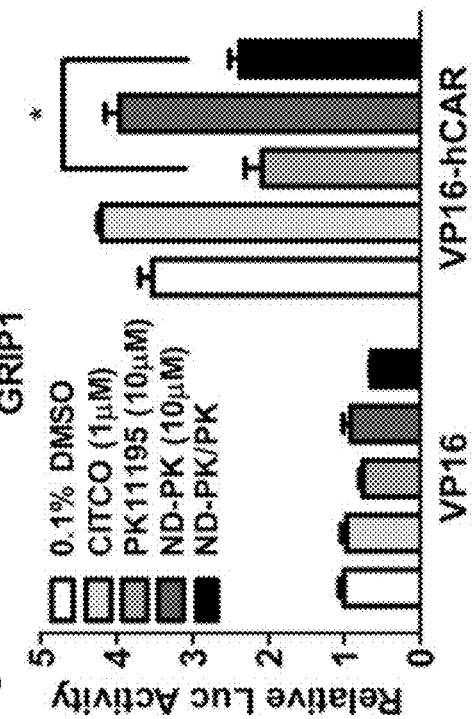
Figure 13C:
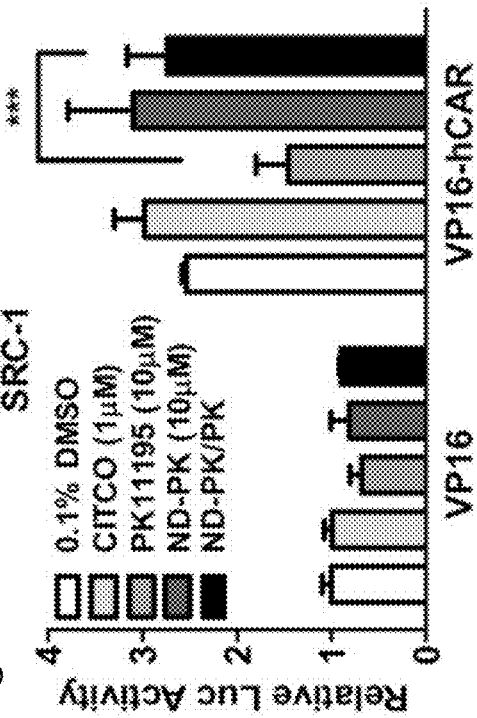
Figure 13E:
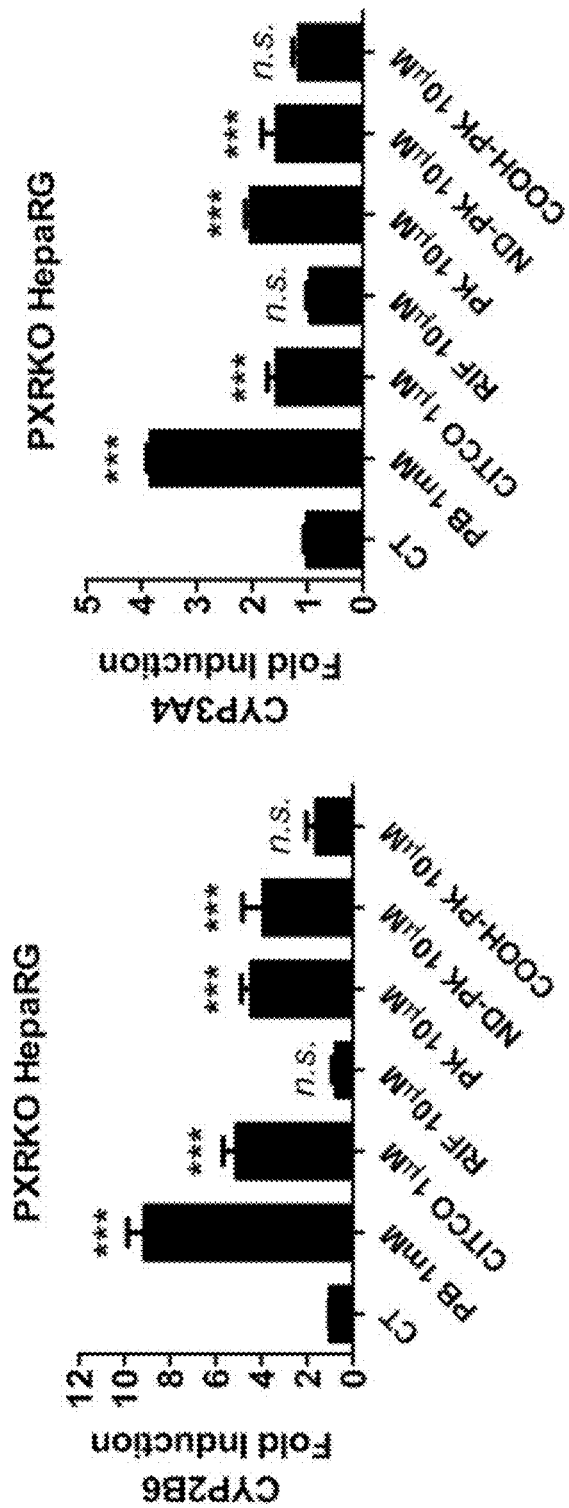
Figure 13F:
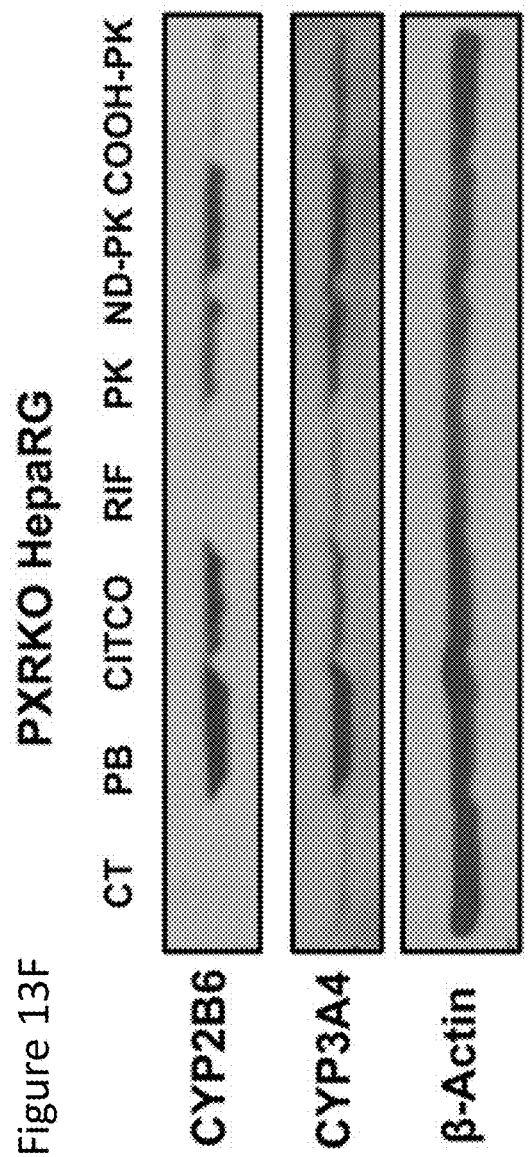

After confirming that COOH-PK and ND-PK were generated in the experimental system, these metabolites were tested for hCAR activation in HepG2-based luciferase assays. As shown in FIG. 13A, ND-PK activated hCAR in a concentration-dependent manner while COOH-PK had no effect on CAR activity. ND-PK activation of hCAR was further confirmed in the CAR1+A/CYP2B6-2.2k reporter assay, where ND-PK robustly activates hCAR to a level similar to the positive control (CITCO), while COOH-PK exhibits negligible CAR activation (FIG. 13B). In separate experiments, the mammalian two-hybrid assay revealed that PK11195 could significantly repress the interaction between hCAR and SRC-1 or GRIP1, while ND-PK moderately enhanced hCAR recruitment of these co-activators in a manner similar to that by CITCO (FIG. 13C, FIG. 13D). Notably, ND-PK markedly rescued PK11195 mediated repression of SRC-1/CAR interaction, while only minimally affecting PK11195-repressed binding of GRIP1 to hCAR. Furthermore, ND-PK significantly induced CYP2B6 and CYP3A4 mRNA and protein expression in the PXR-KO HepaRG cells, indicating that ND-PK can induce P450 expression independent of PXR (FIG. 13E, FIG. 13F). Overall, these results identify ND-PK as the metabolite of PK11195 that is responsible for PK11195 mediated CAR activation in metabolically competent hepatic cells.

ND-PK Induces CYP2B6, CYP3A4 Expression, and Nuclear Translocation of hCAR in HPHs To fully characterize the effect of ND-PK on hCAR activation and target gene induction, HPHs from two liver donors (120 and 121) were treated with multiple concentrations of PK11195, ND-PK, and COOH-PK. The results indicate that ND-PK concentration dependently and potently induced CYP2B6 and CYP3A4 at both mRNA and protein levels, while COOH-PK only exhibited negligible effects on the expression of these genes (FIG. 14A through FIG. 14D). Nuclear translocation of CAR in HPHs has been regarded as the essential step in its activation. To test the nuclear translocation of CAR by PK11195 metabolites, HPHs were infected with adenovirus-expressing EYFP-hCAR overnight before treatment with compounds for 8 hours. Without activation, EYFP-hCAR was predominantly expressed in the cytoplasm of HPHs, and as expected the prototypical CAR activator PB as well as PK11195 induced significant hCAR nuclear accumulation (FIG. 15A, FIG. 15B). Importantly, ND-PK at 10 µM robustly increased nuclear translocation of hCAR, while COOH-PK (10 µM) caused negligible CAR nuclear accumulation, which correlate well with their capacity for P450 induction. These data further support that ND-PK is the metabolite of PK11195 that activates hCAR in physiologically relevant systems.

Computational Modeling of PK11195 and ND-PK

Figure 16A:
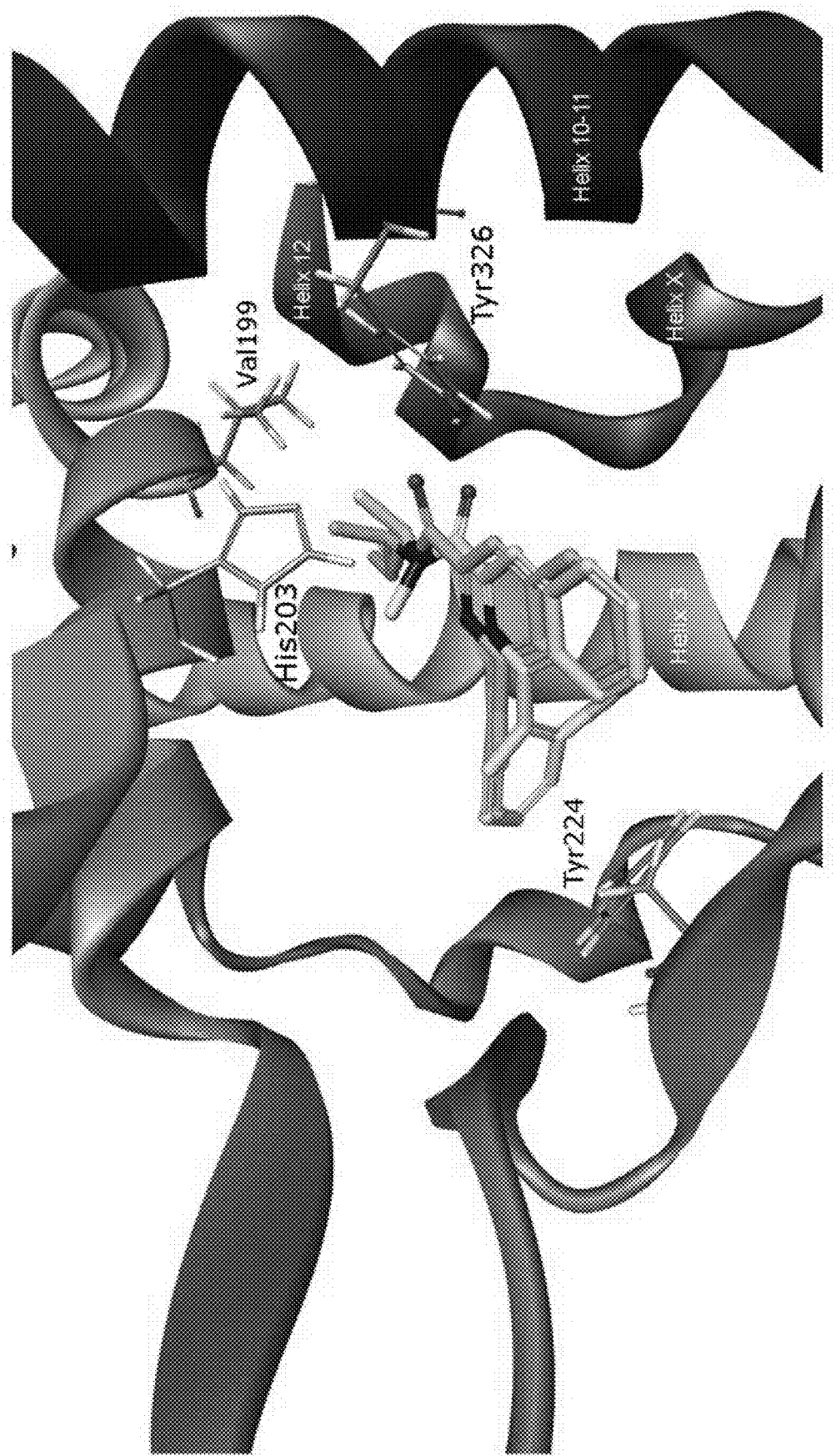
FIG. 16A through FIG. 16E depict the results of experiments demonstrating that N-Demethylation of PK11195 leads to reduced interaction with residues important to CAR activity. The hCAR/ligand-binding domain crystal structure (1XVP) was prepared in Biovia Discovery Studio and docking was carried out using the CDOCKER protocol as detailed in Experimental Example 1. After model validation, PK11195 (yellow) and ND-PK (lightblue) were docked into the CAR ligand-binding pocket (FIG. 16A). Interactions of PK11195 (FIG. 16B), ND-PK (FIG. 16C), CINPA1(FIG. 16D), and CITCO (FIG. 16E) with residues in the ligand-binding pocket of hCAR. Residues are color-coded as follows: dark blue, interact with all structures; light blue, PK11195 and ND-PK; orange, PK11195, CINPAL and CITCO; red, PK11195 and CINPA1; green, CINPA1 and CITCO; yellow, CITCO only; and purple, ND-PK only.
Figure 16B:
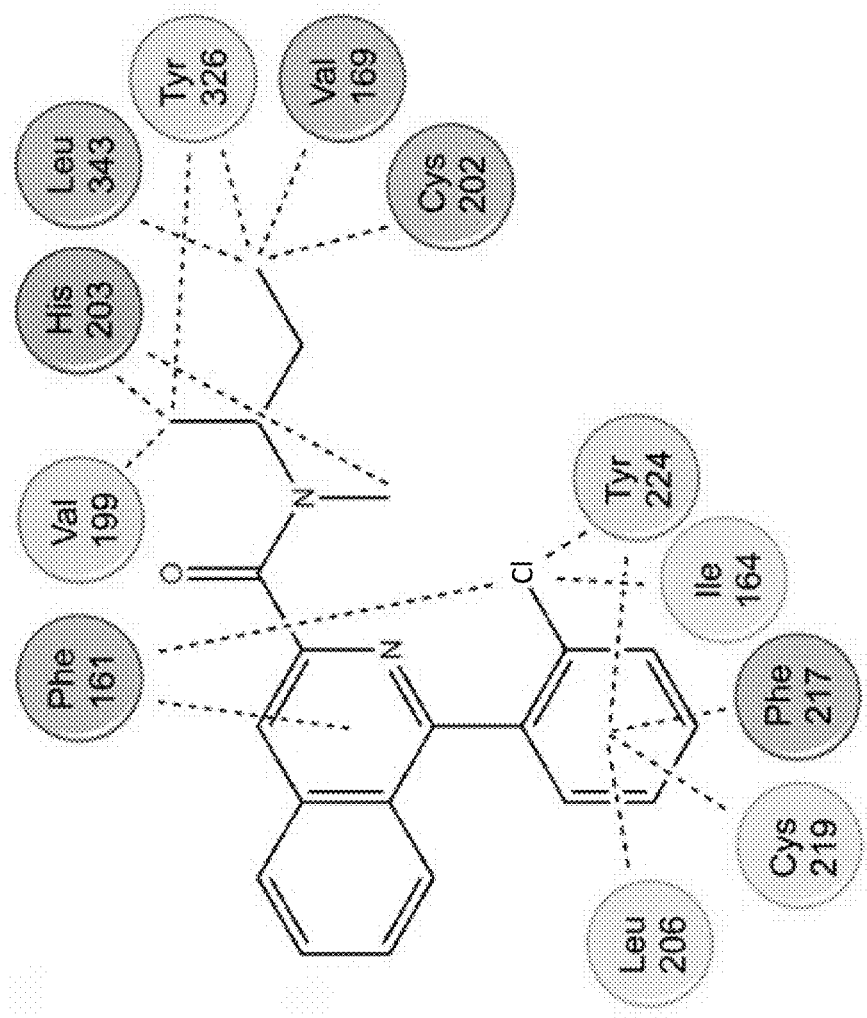
Figure 16C:
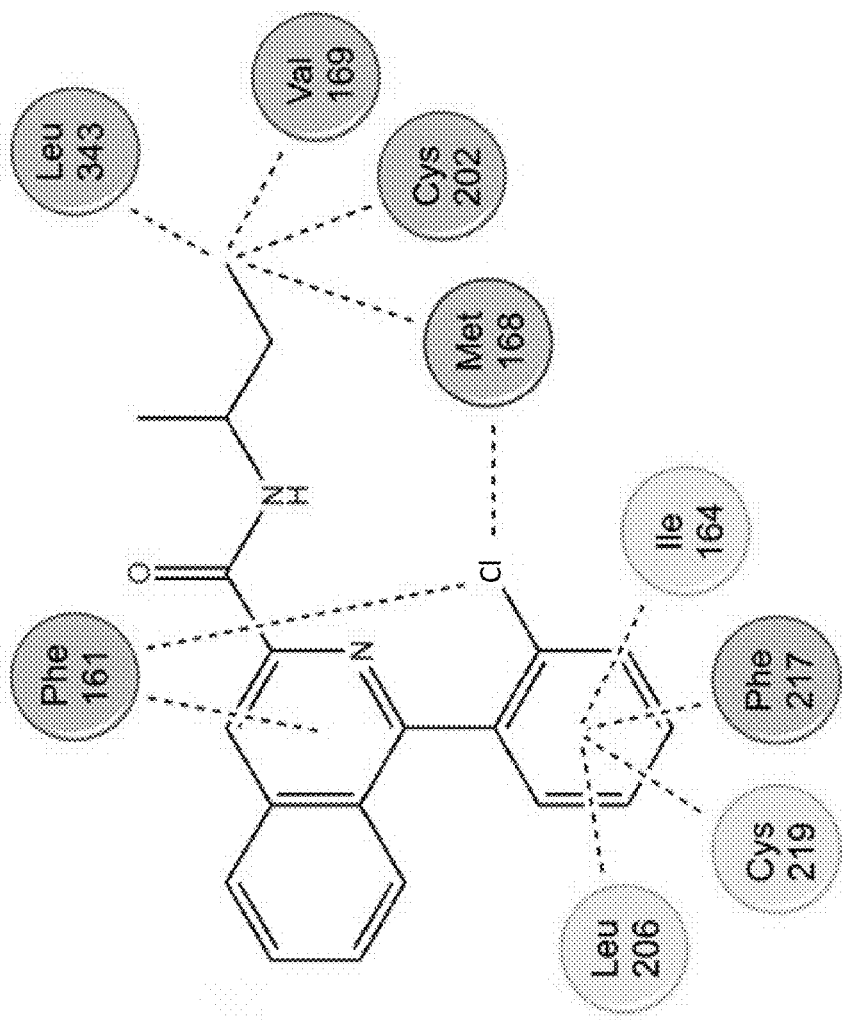
Figure 16D:
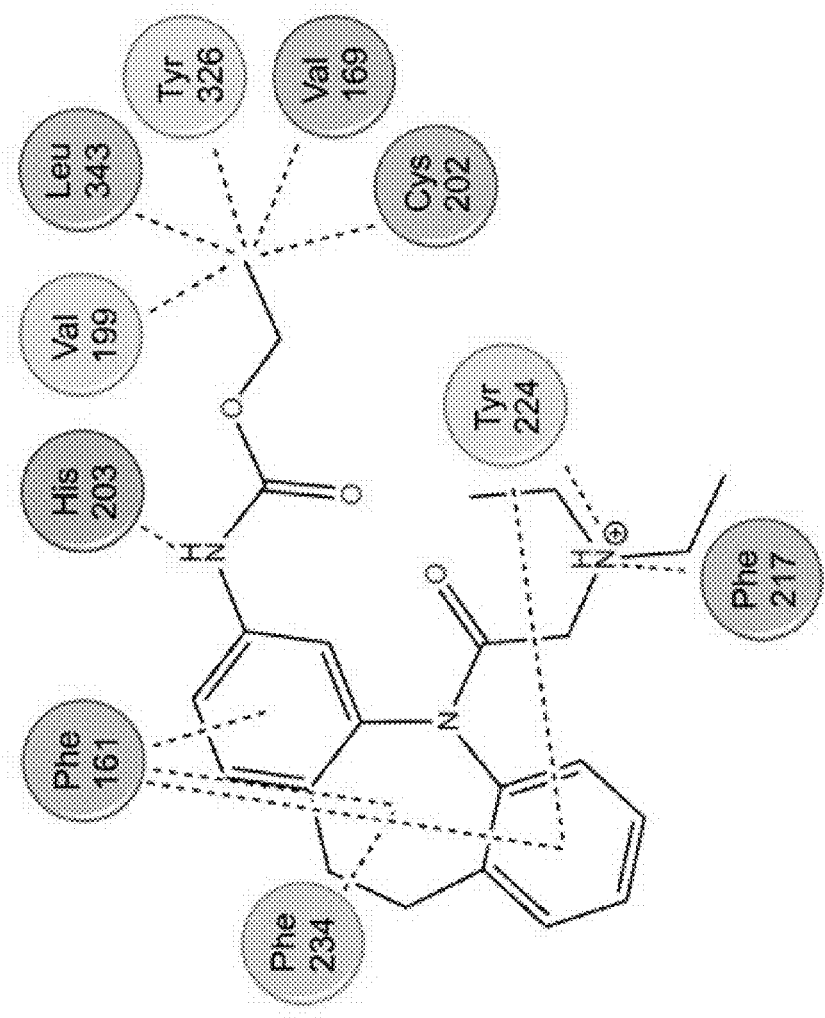
Figure 16E:
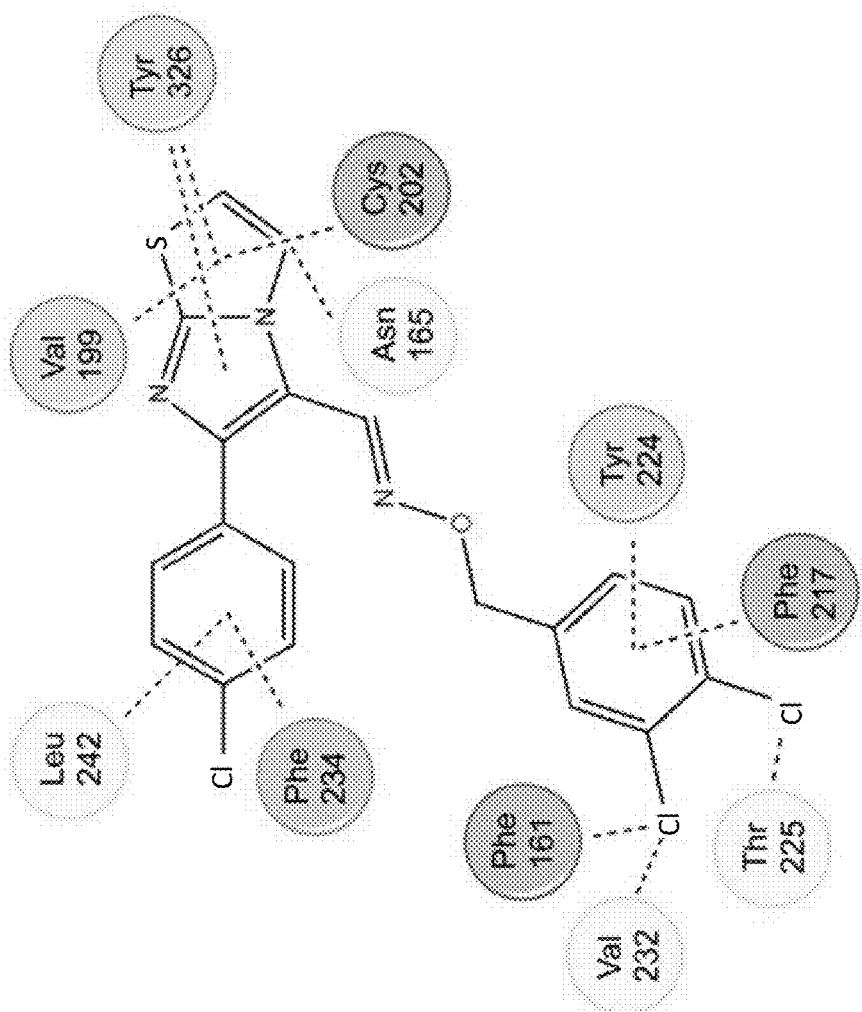

The metabolism of a potent CAR antagonist (PK11195) and its conversion into a potent CAR activator (ND-PK) with a difference of only one methyl group provided a unique opportunity to probe the structure-activity relationship for CAR through molecular modeling. Docking studies used the 1XVP (http:// www.rcsb.org) crystal structure of CITCO bound to the CAR ligand-binding domain to identify PK11195 and ND-PK interactions with different residues in the binding pocket (Xu RX et al., (2004) Mol Cell 16:919-928). Upon validation of the model by docking CITCO into the ligand-binding domain, both PK11195 and ND-PK were docked and found to interact with many of the same residues in the binding pocket, suggesting that they bind in similar conformations (FIG. 16A). However, PK11195 interacts with residues important to CAR activity such as V199, Y224, and Y326, including the N-methyl group interacting with H203, whereas the demethylated form of PK11195 (ND-PK) does not (FIG. 16B, FIG. 16C); notably, PK11195 and the CAR antagonist CINPA1 (FIG. 16D) share these interactions, which may contribute to their antagonism of hCAR (Cherian MT et al., (2016) Drug Metab Dispos 44:1759-1770). The demethylation of PK11195 allows it move away and not interact with these important residues in the CAR binding pocket, which may explain how the difference of one methyl group between PK11195 and ND-PK can have such a substantial effect on CAR activity. These docking studies determined the structure-activity relationship of PK11195 and ND-PK with CAR and demonstrated that even small alterations in ligand structure, such as the demethylation of PK11195, have the potential to alter its interactions with amino acids in the CAR binding pocket and lead to large differences in CAR activity.

The biologic function of CAR is regulated by the interplay between specific cellular factors and small molecular modulators. PK11195, a well-known peripheral benzodiazepine receptor ligand, has been used as a potent hCAR deactivator in cell-based luciferase reporter assays. In contrast to CAR antagonism exhibited in immortalized cell lines, PK11195 robustly induces the expression of both CYP2B6 and CYP3A4 in HPHs, which are prototypical targets for hCAR and hPXR, respectively. The mechanistic basis for this observed discrepancy is largely unknown, although it was presumed that PK11195-mediated P450 induction in HPHs was attributed to its activation of hPXR. Here, PK11195 was shown to significantly induce the expression of CYP2B6 and CYP3A4 in PXR-KO HepaRG cells, which demonstrates that PK11195 can stimulate P450 expression independent of PXR. Utilizing a HPH-HepG2 co-culture model, introduction of metabolically competent HPHs is shown to be sufficient to convert PK11195 from an antagonist to an agonist of hCAR in HepG2 cells. In HPHs, PK11195 is bio-transformed to ND-PK and COOH-PK. Further studies demonstrated that ND-PK is the active metabolite that potently activates hCAR and induces the expression of CYP2B6 and CYP3A4. Moreover, structure activity analysis reveals that N-demethylation of PK11195 allows its side chain to rotate away from residues in the CAR ligand-binding pocket toward a conformation in favor of CAR activation.

CAR and PXR regulate an overlapping array of target genes and share many common chemical modulators (Hernandez JP et al., (2009) Curr Pharmacogenomics Person Med 7:81-105; Mackowiak B and Wang H, (2016) Biochim Biophys Acta 1859:1130-1140). Although such crosstalk between CAR and PXR can be beneficial by forming a defensive network against xenobiotics, it makes the delineation of specific function of each individual receptor extremely challenging, particularly in cells such as HPHs, where both CAR and PXR are abundant and functionally intact. Recently, the HepaRG cell line has emerged as a useful alternative for HPHs; differentiated HepaRG cells exhibit prototypical HPH morphology, inductive expression of major drug-metabolizing enzymes and transporters, and have been used for in vitro drug metabolism and toxicology studies (Josse R et al., (2008) Drug Metab Dispos 36:1111-1118; Andersson TB et al., (2012) Expert Opin Drug Metab Toxicol 8:909-920). The PXR-KO HepaRG cell line provides an excellent model to determine the contribution of CAR/PXR to PK11195-mediated P450 induction. The results uncover an unexpected induction of both CYP2B6 and CYP3A4 by PK11195 in the PXR-KO HepaRG cells, although induction by selective hPXR activator RIF was fully abrogated. These findings provide conclusive evidence that PK11195 can induce CYP2B6/CYP3A4 expression in physiologically relevant hepatic cells independent of hPXR. Indeed, previous and current studies in HPHs have shown that PK11195 induces both CYP2B6 and CYP3A4 in a pattern that mimics that of PB, a dual activator of hCAR and hPXR (Li L et al., (2008) Drug Metab Dispos 37:1098-1106; Anderson LE et al., (2011) Toxicol Lett 202:148-154). Together, these results indicate that PK11195 modulates CAR differently in HPHs and HepaRG cells versus in immortalized cell lines, and is most likely metabolized from an antagonist to an agonist in cells exhibiting physiologically relevant metabolism.

Lack of metabolism capacity is a significant drawback associated with the use of immortalized cell lines in toxicity assessment and drug development. Cell-based luciferase reporter assays using immortalized cell lines in particular have been extensively used to investigate nuclear receptor activity and predict target gene expression. However, proper interpretation of such data has become a heightened concern in both academia and the pharmaceutical industry. Several lines of evidence indicate that introduction of metabolic capacity to cell cultures appears to be an attractive solution to overcome this issue. In this regard, an HPH leukemia/lymphoma cell co-culture model has been previously used to show that the presence of HPHs markedly increases the biotransformation of cyclophosphamide, a chemotherapeutic prodrug, to its pharmacologically active metabolite and leads to enhanced anticancer activity in co-cultured HL-60 and SU-DHL-4 cells (Wang D et al., (2013) Blood 121:329-338; Hedrich WD et al., (2016) Mol Cancer Ther 15:392-401). Using a HPH-HepG2 co-culture system in the current study, PK11195 concentration was observed to dependently increase CAR activation in contrast to decreasing CAR activity when exposed to HepG2 cells only. More importantly, such agonistic effects of PK11195 in the co-culture can be reversed by KET, suggesting that CYP3A4 plays a key role in the metabolism-based conversion of PK11195 in HPHs. It is not uncommon that metabolism can influence the pharmacological action of drugs. For instance, chrysin, a dietary flavonoid, markedly induces the expression and activity of UDP-glucuronosyltransferase 1A1 in HepG2 and Caco-2 cells, but not in HPHs (Smith CM et al., (2005) J Pharmacol Exp Ther 315:1256-1264). Buprenorphine, a potent activator of PXR in HepG2 cells, is not a physiologically relevant activator of PXR or an inducer of associated P450s in HPHs (Li L et al., (2010) J Pharmacol Exp Ther 335:562-571). On the other hand, phenytoin, an antiepileptic agent, is a potent inducer of CYP2B6 and CYP3A4 in HPHs but does not activate CAR or PXR in cell-based reporter assays (Wang H et al., (2004) J Biol Chem 279:29295-29301). Collectively, these studies demonstrate that the metabolic capacity of a cellular system can be a key determinant for the biologic function of a given compound, including its role in nuclear receptor activation.

Previous reports have postulated that PK11195 is rapidly bio-transformed into two major metabolites: the N-desmethyl metabolite, ND-PK, and the amide hydrolysis product, COOH-PK (Roivainen A et al., (2009) Eur J Nucl Med Mol Imaging 36:671-682). In the current study, the activation of hCAR and induction of related P450s was evaluated by both metabolites. Notably, ND-PK significantly increased the luciferase activity of the CYP2B6 reporter by activating hCAR or hCAR1+A in HepG2 cells and induced the expression of CYP2B6 and CYP3A4 in HPHs, HepaRG, and PXR-KO HepaRG cells. In contrast, COOH-PK failed to activate hCAR in HepG2 cells and only marginally induced CYP2B6/CYP3A4 expression in HPHs. Consistent with these observations fluorescent microscopy analysis of adenovirus expressing EYFP-hCAR-infected HPHs further confirmed that ND-PK but not COOH-PK efficiently translocates CAR from the cytoplasm to the nucleus of HPH, the first step in CAR activation. This discovery may also provide a mechanism for the previously observed PK11195-mediated CAR nuclear translocation in HPHs (Li H et al., (2009) Drug Metab Dispos 37:1098-1106). Together, these findings suggest that removing one methyl group from PK11195 changes it from an antagonist to an agonist of CAR and contributes to P450 induction in HPHs.

Mechanistically, ligand binding changes the secondary structure of a nuclear receptor, influences the recruitment of coregulators, and alters the target gene expression thereafter. Previous reports have indicated that nuclear localized CAR can interact with co-activators such as SRC-1 and GRIP1 without the presence of agonists (Muangmoonchai R et al., (2001) Biochem J 355:71-78; Min G et al., (2002) J Biol Chem 277:26356-26363). The mammalian two-hybrid results demonstrate that PK11195-repressed CAR/SRC-1 interaction can be efficiently rescued by ND-PK. However, this recovery is moderate in the CAR/GRIP1 interaction, reflecting the differential capacity between PK11195 and ND-PK in influencing the recruitment of SRC-1 versus GRIP1 by CAR.

Computational modeling studies have shown that the constitutive activity of CAR is mediated by residues in the binding pocket interacting with and stabilizing the activation function 2 (AF2) domain (Andersin T et al., (2003) Mol Endocrinol 17:234-246; Xu RX et al., (2004) Mol Cell 16:919-928; Windshügel B et al., (2005) J Mol Model 11:69-79). Agonists tend to bind and further stabilize the AF2 domain in the active conformation, while antagonists disrupt its stability (Jyrkkärinne J et al., (2008) J Med Chem 51:7181-7192). To explore how the N-demethylation of PK11195 has such a drastic effect on CAR activity, docking studies were used to probe the structure-activity relationship of PK11195 and ND-PK with CAR. Although both compounds bound in similar conformations, PK11195 interacted with residues important to CAR activation, such as V199, H203, Y224, and Y326, while ND-PK does not. Residues V199 and Y326 are thought to stabilize the CAR AF2 domain in the active conformation by interacting with H12, while Y224 may be involved in local protein folding. Mutating any of these residues abrogates the basal activity of CAR while mutating H203 reduces CAR activity by 50%, demonstrating the importance of these residues to CAR activity (Jyrkkarinne J et al., (2005) J Biol Chem 280:5960-5971). Therefore, PK11195 interactions with these residues may destabilize the AF2 domain, while loss of the N-methyl group in ND-PK could restabilize H12. Indeed, the potent CAR antagonist CINPA1 also interacts with these residues, suggesting such interactions are important in CAR antagonism (Cherian MT et al., (2016) Drug Metab Dispos 44:1759-1770). CITCO interacts with V199, Y224, and Y326, but the interaction distances are generally greater than those of PK11195 or CINPA1 and thus may not displace these residues enough to inhibit stabilization of H12. Although docking studies provide a possible mechanism for this drastic change in CAR activity, future studies will use molecular dynamics and mutagenesis to further probe the detailed structure-activity relationship between PK11195 and ND-PK with CAR.

In conclusion, this study demonstrates that PK11195 is metabolically converted from an antagonist to an agonist of hCAR and this conversion contributes significantly to the observed induction of CYP2B6 and CYP3A4 in HPHs and HepaRG cells. It is shown that ND-PK is the metabolite responsible for PK11195-mediated CAR activation by facilitating CAR interactions with SRC-1 and GRIP1 and enhancing CAR nuclear translocation in HPHs. The demethylation of PK11195 also disrupts its interaction with residues critical to CAR activity, providing a possible mechanism for the activity shift. Additionally, this report highlights the importance of metabolic competence when attempting to identify modulators of nuclear receptors and provides a possible solution to this problem with a novel HPH co-culture system.

Example 2: Toxicity Test

Figure 17:
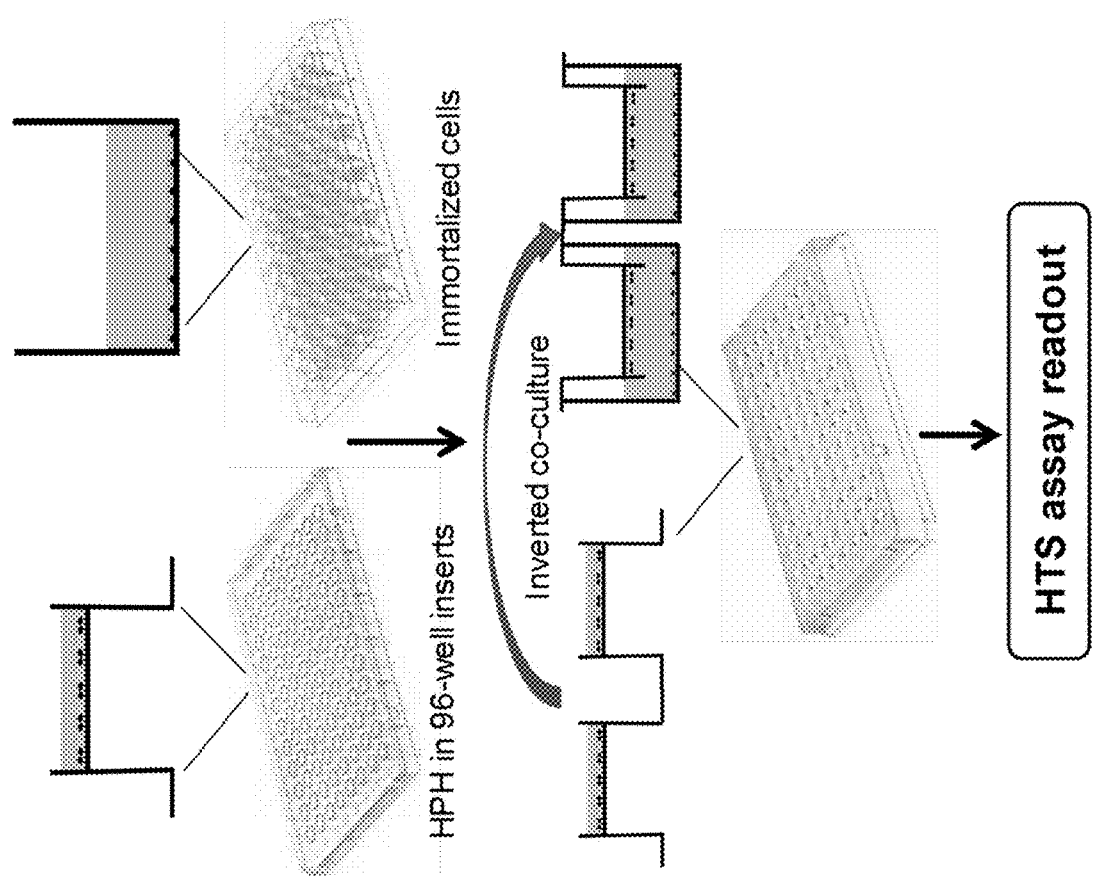
FIG. 17 depicts a schematic illustration of an HPH-cell line co-culture. The depicted inverted co-culture design maximizes the exposure of metabolites to target cells.

Lack of metabolic competence is a major limitation for the majority of current high-throughput (HTS) assays used for evaluation of chemical safety. Properly-cultured human primary hepatocyte (HPH) retaining physiologically-relevant expression and function of major drug-metabolizing enzymes and transporters have been well-accepted as an in vitro model for testing xenobiotic metabolism and toxicity. Several liver-derived models including liver slices, immortalized hepatic cell lines, microsomes and S9 cell fractions, and primary hepatocytes have been used for studying xenobiotic metabolism and potential toxicity in vitro. Each model is associated with specific limitations, such as the short-term viability of liver slices or the relatively low expression of drug-metabolizing enzymes in immortalized cell lines. Comparatively, HPH cultured in a sandwich configuration represent an in vitro model that closely resembles the in vivo human hepatic phenotypes. Sandwich-cultured HPH maintain the complete complement of drug-metabolizing enzymes and transporter proteins, while prolonging the longevity of cultures. The following study demonstrates a HPH-target cell co-culture model that can be scaled up to a HTS format, adding physiologically-relevant metabolism to most currently used cell-based screening assays. As depicted in the schematic diagram (FIG. 17, exemplified in a 96-well platform), HPH are plated in the top chamber of the newly-designed 96-well Inverted Co-culture System insert, while existing cell lines used in ToxCast and Tox21 HTS assays are plated on the bottom of the 96-well plate. After cell attachment, the HPH-containing co-culture inserts are flipped over into the plate containing target cells to complete the inverted co-culture model. To overcome the metabolic variability among liver donors, pooled plateable cryopreserved HPH (Bioreclamation, IVT, Baltimore, Md.) are seeded onto the collagen-coated insert in complete William's E medium as described previously (Faucette SR et al., (2007) J Pharmacol Exp Ther 320:72-80). Twelve hours after seeding, hepatocytes are overlaid with Matrigel (0.25 µg/ml) to form HPH sandwich culture configuration, which improves the metabolic function of hepatocytes. Immortalized cells are plated in 96-well plates at cell densities according to the screening assay protocol. On day two, HPH-containing co-culture inserts are transferred to the cell line-seeded 96-well plate and treated with test compounds for another 24 h. Subsequently, the 96-well plates are subjected to HTS assay readouts. To this end, proof-of-concept experiments have been completed, including: 1) the design and 3D printing of the inverted co-culture insert; 2) an assay to determine the metabolic capacity of HPHs in this culture model using common metabolism probes; and 3) functionally characterization of the co-culture model by determining the metabolic-dependence of the toxicity of 3 model compounds.

The materials and methods are now described.

All cytotoxicity compounds were obtained from the U.S. Environmental Protection Agency. Corning HTS Transwell 96-well receiver plates (cat. #CLS3382), additional cyclophosphamide (CPA), 3-(4,5-dimethylthiazol-2-yl)-2,5-diphenyltetrazolium bromide (MTT), and oridonin were obtained from Sigma-Aldrich (St. Louis, Mo.). CellTiterGlo reagent was obtained from Promega (Madison, Wis.).

Design and 3D Printing 96-Well Cell Culture Insert

Figure 18:
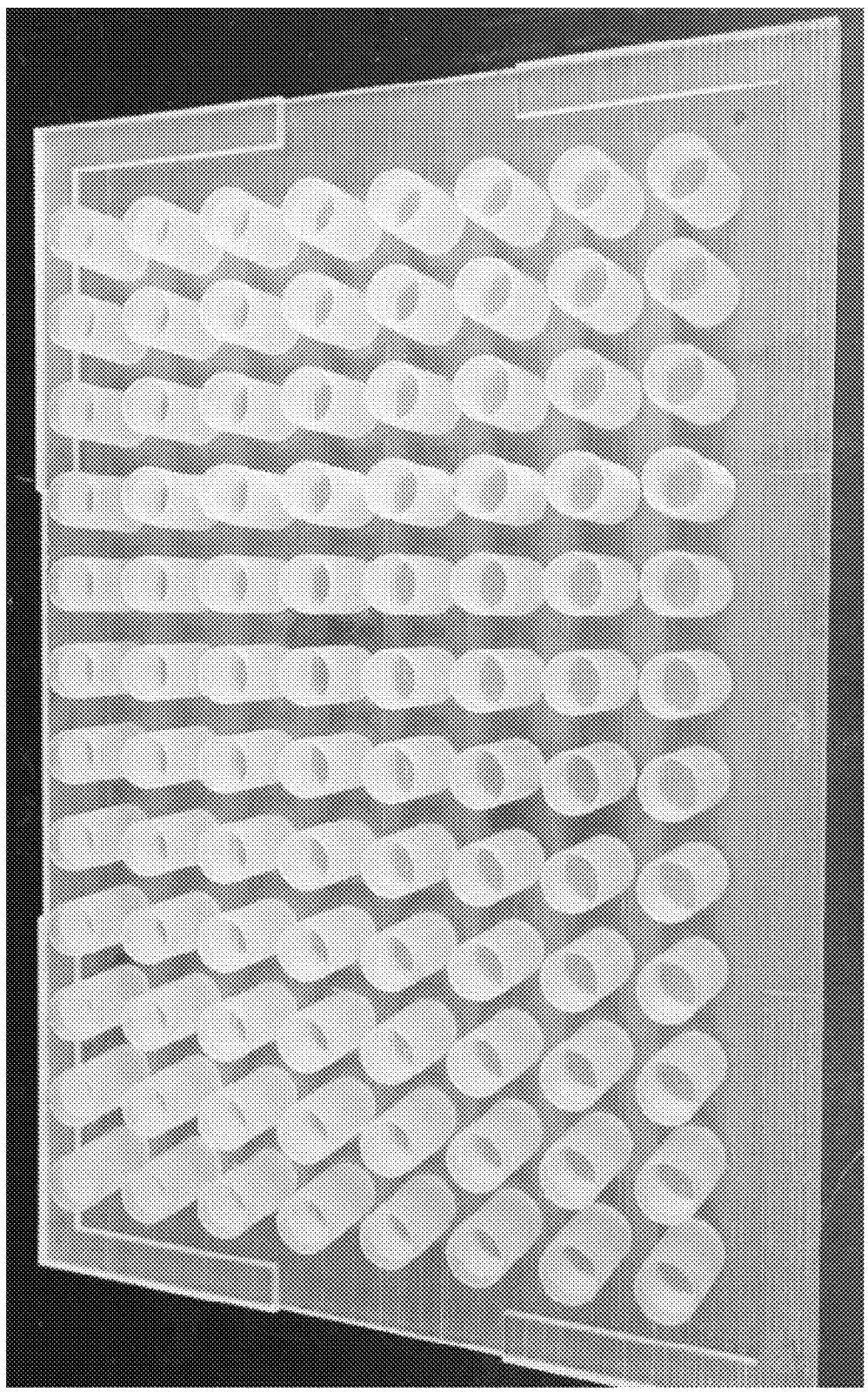
FIG. 18 depicts a printed 96-well inverted co-culture insert prototype.
Figure 19:
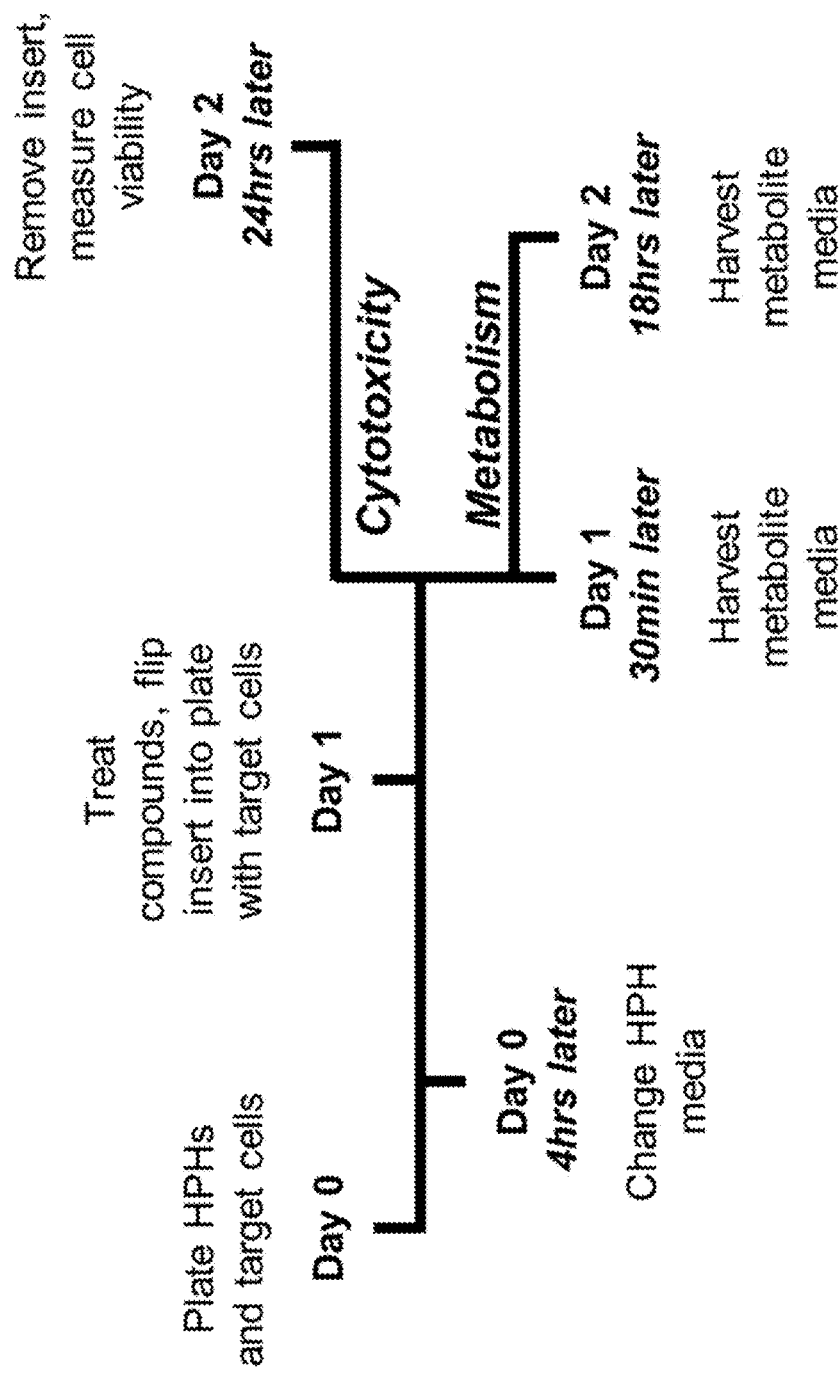
FIG. 19 depicts a schematic chart for cell culture and sample harvesting using the co-culture inserts.

The inverted co-culture system 3D-model was designed using Autodesk TinkerCAD (San Rafael, Calif.). The insert was designed to fit into Corning HTS Transwell base plates, enabling automation. The prototype design is amenable to including access ports for each well, enabling automated sample collection and media addition. After the inverted co-culture system 3D-design was completed (FIG. 2), it was sent to Potomac Photonics (Baltimore, Md.) for printing. The 3D model was printed on a ProJet 300HD using EX200 filament for the plate and S100 filament for dissolvable supports (FIG. 18), all obtained from 3D Systems (Rock Hill, S.C.). The EX200 filament is optically translucent and is USP Class VI certified for use in biomedical devices.

Culture of HPH in 3D Printed Insert and Metabolic Activity Measurement

Cryopreserved or fresh HPH were obtained from Bioreclamation IVT. Hepatocytes over 90% viability were seeded in the collagen-coated inverted co-culture insert at a volume of 40 µL at 50,000 cells/well and incubated at 37° C. and 5% $CO_2$. After cell attachment for 4 hrs, seeding media was changed to serum-free William's E Medium supplemented with insulin, transferrin, and selenium, 0.1 µM dexamethasone, 100 U/ml penicillin, and 100 µg/ml streptomycin and HPHs were incubated overnight. HEK-293 cells for the cytotoxicity assay were also plated at a density of 5,000 cells/well in a 96-well Transwell base plate and cultured overnight. Subsequently, cells were exposed to culture media containing different concentration of test compounds (treatment media). For the co-culture, 40 µL it of treatment media was added to each insert and 120 µL was added to the base well, after flipping over the co-culture contains a total volume of 160 µL treatment media per well. For metabolism studies, substrates were added to the culture at the recommended concentrations (100 µM terfenadine, 100 µM phenacetin, 500 µM bupropion, 200 µM chlorzoxazone, and 500 µM 7-hydroxycoumarin) and 100 µL of William's E treatment media per well and was harvested at 30 min or 18 hrs after substrate exposure.

Cytotoxicity Assays in Inverted Co-Culture Model

For cytotoxicity studies, the HPH/HEK-293 co-culture was incubated with treatment media (DMEM containing 10% FBS+test compounds) for 24 hrs. Oridonin (100 µM) was used as a positive control. To correlate results with previous studies, cyclophosphamide (CPA) was treated at 1000, 750, 500, 250, 125, 100, 50, and 10 µM, while doxorubicin (DOX) and benzo[a]pyrene (BaP) were treated at the recommended concentrations. To measure cell viability, the insert and media were removed and 100 µL of a 50:50 media:CellTiterGlo mix or media containing 1 mg/mL MTT was added to each well of the plate. The luminous-activity for the CellTiterGlo assay was measured on a Promega GloMax 96-well microplate luminometer (Madison, Wis.) following the manufacturer's instructions. For the MTT assay, cells were incubated with MTT solution for 2 hrs before media was removed from the plate, 100 µL of DMSO was added to each well, the plate was shaken for 15 min, and absorbance was measured at 490 nm and 650 nm (background).

The results are now described.

Metabolic Activity of the Co-Culture Model

To determine the metabolic competence of the HPH co-culture, probe substrates for CYP3A4, 1A2, 2B6, 2E1, and UGTs were incubated with the co-culture for 30 min or 18 hrs. HPHs were seeded at 50,000 cells/well. The co-culture insert with HPHs (Insert), no cell control (IC), and HPHs in a normal 96-well plate (CT) were treated with either 100 µM terfenadine (TERF), 100 µM phenacetin (PHEN), 500 µM bupropion (BUP), 200 µM chlorzoxazone (CHLZ), and 500 µM 7-hydroxycoumarin (7-HC) in complete William's E medium for 30 min or 18 hrs (FIG. 20). At that time, media was harvested and added to a plate either alone or with acetonitrile (ACN).

Metabolism-Based Cytotoxicity in the Co-Culture Model

Figure 21A:
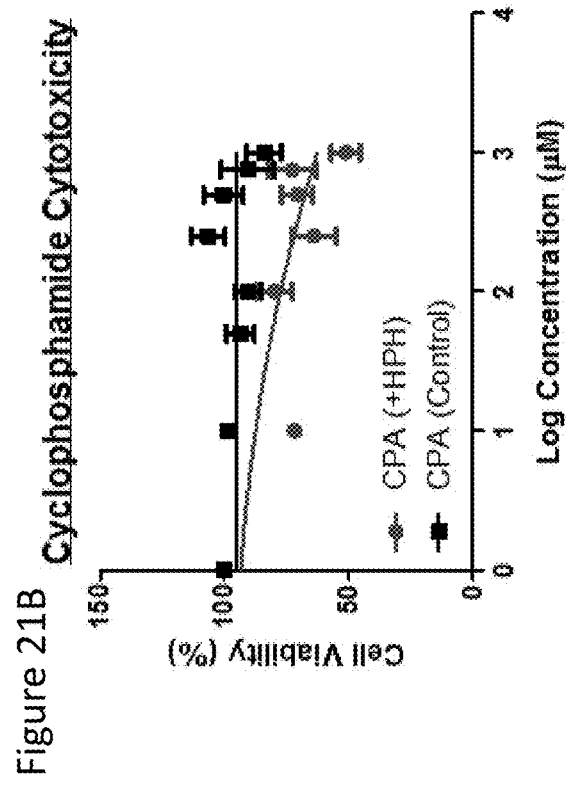
FIG. 21A through FIG. 21C depict the results of experiments demonstrating metabolism-dependent toxicity of (FIG. 21A) doxorubicin, (FIG. 21B) cyclophosphamide, and (FIG. 21C) benzo[a]pyrene in the HPH co-culture model.
Figure 21B:
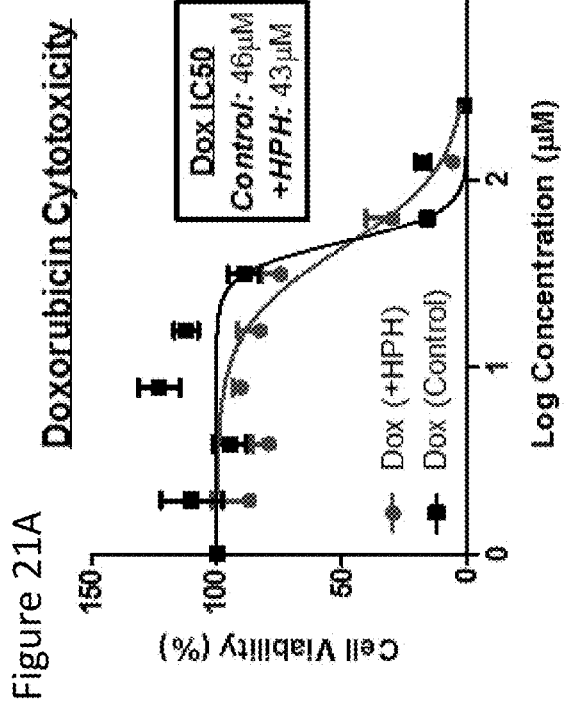
Figure 21C:
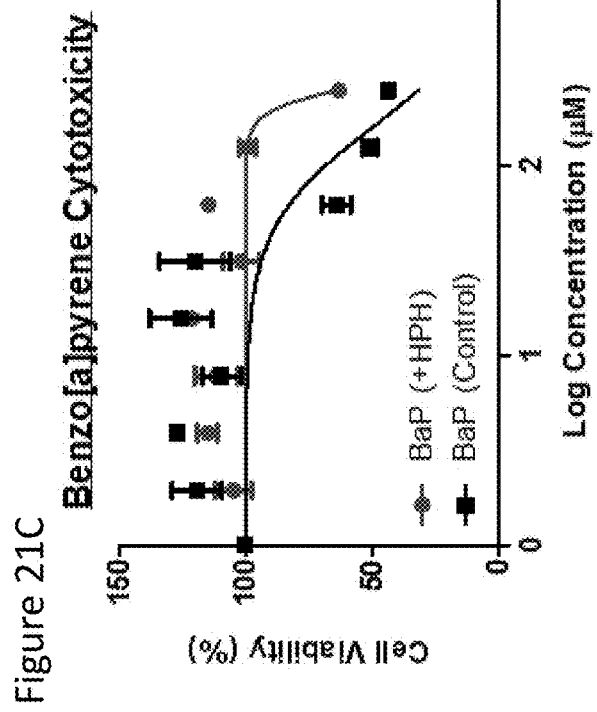

To determine whether HPH in the Inverted Co-culture System provide suitable metabolism for physiologically-relevant cytotoxicity assays, HEK-293 cells were treated with cyclophosphamide (CPA), benzo[a]pyrene (BaP), or doxorubicin (DOX) at the indicated concentrations. As doxorubicin is poorly metabolized and over 50% is eliminated from the body unchanged (Mordente A et. al, (2009) Current Medicinal Chemistry 16:1656-1672), doxorubicin is not expected to have metabolism-dependent toxicity in the co-culture system. Indeed, the data exhibit no significant difference in the IC50s of DOX between the HPH/HEK-293 co-culture (43 µM) and control (HEK-293) groups (46 µM) (FIG. 21A). On the other hand, CPA showed metabolism-dependence in the co-culture only, while there is no cytotoxicity to HEK-293 cultured alone at the concentration up to 1 mM (FIG. 21B). These results are consistent with previous reports using HPH/leukemia or HPH/lymphoma co-cultures, indicating that as a prodrug the cytotoxicity of CPA relies on hepatic metabolism (Hedrich WD et al., (2016) Mol Cancer Ther 15:392-401; Wang D et al., (2013) Blood 121:329-338). Interestingly, benzo[a]pyrene (BaP) showed a trend of detoxification when co-cultured with HPH (FIG. 21C). Although current literature shows that the diol metabolites of BaP are more carcinogenic than the parent compound, the metabolites of BaP might be less toxic in an acute toxicology end point.

Ease of Use

The inverted co-culture system is configured to integrate into existing HTS assays and provide a simple solution to a complex problem. Compared with the Transwell® culture plates, the inverted co-culture system significantly increases attachment and morphology of HPH cells, while allowing the HPH and target cells to directly face each other and enhance the exchange of medium and metabolites in the same chamber.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

The appended claims are intended to be construed to include all such embodiments and equivalent variations.

What is claimed is:

1. A culture well insert, comprising:
a planar substrate;
at least one sidewall extending perpendicularly from the substrate to form an open top chamber within a perimeter of the at least one sidewall; and
a non-permeable well bottom surface positioned-within the open top chamber of the at least one sidewall and between the open top of the chamber and the substrate, wherein the well bottom surface and the at least one sidewall form a fixed single unit.

2. The culture well insert of claim 1, wherein the open top chamber has a cross-sectional shape selected from the group consisting of a circle, an oval, a square, a rectangle, a triangle, a pentagon, a hexagon, an octagon and an irregular shape.

3. The culture well insert of claim 1, further comprising at least one slit in the at least one sidewall extending from the rim of the open top of the chamber opposite the substrate to the well bottom surface.

4. The culture well insert of claim 1, further comprising at least one aperture in the at least one sidewall positioned between the open top of the chamber and the well bottom surface.

5. The culture well insert of claim 1, further comprising at least one access port in the substrate, wherein the access port is adjacent the at least one sidewall.

6. The culture well insert of claim 1, further comprising at least one access port formed within a portion of the at least one sidewall.

7. The culture well insert of claim 1, wherein the substrate further comprises a raised lip along at least a portion of a perimeter of the substrate.

8. A culture well insert arras, comprising:
a planar substrate; and
a plurality of well inserts, each well insert comprising at least one sidewall extending perpendicularly from the substrate to form an open top chamber within a perimeter of the at least one sidewall, and a non-permeable well bottom surface positioned within the open top chamber of the at least one sidewall and between the open top of the chamber and the substrate, wherein the well bottom surface and the at least one sidewall form a fixed single unit.

9. The culture well insert array of claim 8, wherein the open top chamber of each well insert has a cross-sectional shape selected from the group consisting of a circle, an oval, a square, a rectangle, a triangle, a pentagon, a hexagon, an octagon and an irregular shape.

10. The culture well insert array of claim 8, wherein each well insert further comprises at least one slit in the at least one sidewall extending from the rim of the open top of the chamber opposite the substrate to the well bottom surface.

11. The culture well insert array of claim 8, wherein each well insert further comprises at least one aperture in the at least one sidewall positioned between the open top of the chamber and the well bottom surface.

12. The culture well insert array of claim 8, wherein each well insert further comprises at least one access port in the substrate, wherein each access port is adjacent the at least one sidewall of each well insert, respectively.

13. The culture well insert array of claim 8, wherein each well insert further comprises at least one access port formed within a portion of the at least one sidewall of each well insert, respectively.

14. The culture well insert array of claim 8, wherein the substrate further comprises a raised lip along at least a portion of a perimeter of the substrate.

\* \* \* \* \*